(12) United States Patent
Mullins et al.

(10) Patent No.: US 11,197,977 B2
(45) Date of Patent: Dec. 14, 2021

(54) CATHETERS AND DEVICES AND SYSTEMS INCORPORATING SUCH CATHETERS

(71) Applicant: Perfuze Limited, Dangan (IE)

(72) Inventors: Liam Mullins, Galway (IE); Dara Finneran, County Roscommon (IE); Alejandro Espinosa, Miami, FL (US); Lisandro Rivera, Miramar, FL (US); Robert Farnan, Fort Lauderdale, FL (US); Brett Naglreiter, Miramar, FL (US); John Logan, Plymouth, MN (US); Andrew Cragg, Edina, MN (US)

(73) Assignee: Perfuze Limited, Galway (IE)

( * ) Notice: Subject to any disclaimer, the term of this patent is extended or adjusted under 35 U.S.C. 154(b) by 0 days.

(21) Appl. No.: 16/817,787

(22) Filed: Mar. 13, 2020

(65) Prior Publication Data
US 2020/0206458 A1 Jul. 2, 2020

Related U.S. Application Data

(63) Continuation of application No. PCT/EP2018/085064, filed on Dec. 14, 2018.
(Continued)

(51) Int. Cl.
*A61M 25/00* (2006.01)
*A61B 17/22* (2006.01)
(Continued)

(52) U.S. Cl.
CPC ......... *A61M 25/0054* (2013.01); *A61B 17/22* (2013.01); *A61L 29/06* (2013.01);
(Continued)

(58) Field of Classification Search
CPC .......... A61M 25/0054; A61M 25/0108; A61M 25/0012; A61M 25/005
See application file for complete search history.

(56) References Cited

U.S. PATENT DOCUMENTS 4,463,755 A * 8/1984 Suzuki ................. A61M 16/08
                                                                128/200.18
4,784,639 A    11/1988 Patel
(Continued)

FOREIGN PATENT DOCUMENTS

EP    0421650 A1    4/1991
EP    0 861 674 A1    9/1998
(Continued)

OTHER PUBLICATIONS

Nov. 4, 2019 International Search Report and Written Opinion issued in International Patent Application No. PCT/EP2018/085064.

*Primary Examiner* — Bradley J Osinski
(74) *Attorney, Agent, or Firm* — Bookoff McAndrews, PLLC

(57) ABSTRACT

A catheter has a jacket (10, 11, 5) defining a lumen and a helical support (6). The catheter has a proximal portion (1) and a distal portion (3), the distal portion having for at least some of its length a corrugated outer surface. A transition portion has a flexural stiffness which is less than that of the distal portion and more than that of the proximal portion. The transition portion provides an optimum transition in flexural stiffness by way of features of the jacket including geometry of jacket corrugations (15), or overlapping tubular layers (1073, 1074). The distal end of the distal portion may have an extension of liner material folded over (1072, 1082) to provide a particularly soft tip. In other examples the liner is terminated (763) before the distal tip. The catheter is particularly suited to an aspiration device (1350) with a flow restrictor (1353) and the distal portion distal of the flow restrictor. An aspiration system (3500) may employ the catheter with a pump which dynamically applies negative or positive pressure to optimally aspirate a clot.

21 Claims, 22 Drawing Sheets

Related U.S. Application Data

(60) Provisional application No. 62/616,188, filed on Jan. 11, 2018, provisional application No. 62/599,573, filed on Dec. 15, 2017, provisional application No. 62/599,560, filed on Dec. 15, 2017.

(51) Int. Cl.
*A61L 29/06* (2006.01)
*A61M 25/01* (2006.01)

(52) U.S. Cl.
CPC ...... *A61M 25/005* (2013.01); *A61M 25/0012* (2013.01); *A61M 25/0108* (2013.01); *A61B 2017/22067* (2013.01); *A61B 2017/22079* (2013.01)

(56) References Cited

U.S. PATENT DOCUMENTS

| | | | |
|---|---|---|---|
| 5,256,233 A * | 10/1993 | Winter | B29D 23/001 156/244.13 |
| 5,358,493 A | 10/1994 | Schweich et al. | |
| 5,454,795 A * | 10/1995 | Samson | A61L 29/049 604/526 |
| 5,460,170 A | 10/1995 | Hammerslag | |
| 5,507,995 A | 4/1996 | Schweich et al. | |
| 5,697,970 A * | 12/1997 | Schmitt | A61F 2/06 623/1.35 |
| 5,700,253 A | 12/1997 | Parker | |
| 5,865,723 A | 2/1999 | Love | |
| 5,873,866 A | 2/1999 | Kondo et al. | |
| 5,876,386 A | 3/1999 | Samson | |
| 5,879,342 A | 3/1999 | Kelley | |
| 5,938,587 A * | 8/1999 | Taylor | A61B 1/018 138/118 |
| 5,951,539 A | 9/1999 | Nita et al. | |
| 5,980,505 A | 11/1999 | Wilson | |
| 6,004,310 A | 12/1999 | Bardsley et al. | |
| 6,171,297 B1 | 1/2001 | Pederson et al. | |
| 6,217,566 B1 | 4/2001 | Ju et al. | |
| 6,358,238 B1 | 3/2002 | Sherry | |
| 6,464,632 B1 | 10/2002 | Taylor | |
| 6,464,684 B1 | 10/2002 | Galdonik | |
| 6,482,171 B1 | 11/2002 | Corvi et al. | |
| 6,508,806 B1 | 1/2003 | Hoste | |
| 6,616,651 B1 | 9/2003 | Stevens | |
| 6,652,508 B2 | 11/2003 | Griffin et al. | |
| 6,689,120 B1 | 2/2004 | Gerdts | |
| 6,709,429 B1 | 3/2004 | Schaefer et al. | |
| 6,824,553 B1 | 11/2004 | Samson et al. | |
| 6,858,024 B1 * | 2/2005 | Berg | A61M 25/0013 604/525 |
| 7,001,369 B2 | 2/2006 | Grifffin et al. | |
| 7,273,485 B2 | 9/2007 | Simpson et al. | |
| 7,674,239 B2 | 3/2010 | Sisken et al. | |
| 7,704,245 B2 | 4/2010 | Dittman et al. | |
| 7,815,599 B2 | 10/2010 | Griffin et al. | |
| 7,815,608 B2 | 10/2010 | Schafersman et al. | |
| 7,815,762 B2 | 10/2010 | Lentz et al. | |
| 7,914,466 B2 | 3/2011 | Davis et al. | |
| 8,021,352 B2 | 9/2011 | Slazas et al. | |
| 8,070,898 B2 | 12/2011 | Eversull et al. | |
| 8,092,374 B2 | 1/2012 | Smith et al. | |
| 8,114,144 B2 | 2/2012 | Chow et al. | |
| 8,292,802 B2 | 10/2012 | Smith et al. | |
| 8,343,136 B2 | 1/2013 | Howat et al. | |
| 8,366,699 B2 | 2/2013 | Jimenez et al. | |
| 8,454,571 B2 | 6/2013 | Leeflang et al. | |
| 8,486,048 B2 | 7/2013 | Kubo et al. | |
| 8,523,899 B2 | 9/2013 | Suzuki | |
| 8,591,495 B2 | 11/2013 | Fischell et al. | |
| 8,608,690 B2 | 12/2013 | Pal | |
| 8,636,716 B2 | 1/2014 | Griffin et al. | |
| 8,652,098 B2 | 2/2014 | Haslinger | |
| 8,663,196 B2 | 3/2014 | Kassab et al. | |
| 8,663,197 B2 | 3/2014 | Ogura et al. | |
| 8,702,680 B2 | 4/2014 | Jimenez et al. | |
| 8,708,997 B2 | 4/2014 | Parker | |
| 8,715,441 B2 | 5/2014 | Brustad et al. | |
| 8,734,699 B2 | 5/2014 | Heideman et al. | |
| 8,870,790 B2 | 10/2014 | Davis et al. | |
| 8,926,560 B2 | 1/2015 | Dinh et al. | |
| 9,022,977 B2 | 5/2015 | Rosenman et al. | |
| 9,119,740 B2 | 9/2015 | Cannon et al. | |
| 9,339,629 B2 | 5/2016 | Watanabe et al. | |
| 9,352,123 B2 | 5/2016 | Zhou et al. | |
| 9,365,018 B2 | 6/2016 | Drewes, Jr. et al. | |
| 9,370,639 B2 | 6/2016 | Plassman et al. | |
| 9,339,114 B2 | 7/2016 | Parker | |
| 9,393,380 B2 | 7/2016 | Merk et al. | |
| 9,597,481 B2 | 3/2017 | Ishikawa | |
| 2001/0034514 A1 | 10/2001 | Parker | |
| 2002/0058910 A1 | 5/2002 | Hermann et al. | |
| 2002/0132076 A1 | 9/2002 | Stevens | |
| 2002/0156460 A1 | 10/2002 | Ye et al. | |
| 2003/0135198 A1 | 7/2003 | Berhow et al. | |
| 2004/0220549 A1 | 11/2004 | Dittman et al. | |
| 2004/0243102 A1 | 12/2004 | Berg et al. | |
| 2005/0165366 A1 | 7/2005 | Brustad et al. | |
| 2006/0030835 A1 | 2/2006 | Sherman et al. | |
| 2006/0200110 A1 | 9/2006 | Lentz et al. | |
| 2006/0229589 A1 | 10/2006 | Itou et al. | |
| 2006/0259118 A1 | 11/2006 | Pal et al. | |
| 2007/0225680 A1 | 9/2007 | Biggin et al. | |
| 2008/0108974 A1 | 5/2008 | Yee Roth | |
| 2008/0119825 A1 | 5/2008 | Imai et al. | |
| 2009/0149834 A1 | 6/2009 | Moss | |
| 2009/0236770 A1 | 9/2009 | Fogarty | |
| 2009/0240236 A1 | 9/2009 | Fogarty | |
| 2010/0049167 A1 | 2/2010 | Myers | |
| 2010/0145313 A1 | 6/2010 | Packard | |
| 2010/0180976 A1 | 7/2010 | Witz et al. | |
| 2011/0112567 A1 | 5/2011 | Lenker et al. | |
| 2011/0245775 A1 | 10/2011 | Tekulve | |
| 2011/0288532 A1 | 11/2011 | Faherty et al. | |
| 2011/0319754 A1 | 12/2011 | Solar et al. | |
| 2012/0078187 A1 | 3/2012 | Delap | |
| 2012/0277729 A1 | 11/2012 | Melsheimer | |
| 2013/0090632 A1 | 4/2013 | Tahara et al. | |
| 2013/0095228 A1 | 4/2013 | Howat et al. | |
| 2014/0046297 A1 | 2/2014 | Shimada et al. | |
| 2015/0174364 A1 | 6/2015 | Kennelly et al. | |
| 2015/0217083 A1 | 8/2015 | Richter et al. | |
| 2015/0273184 A1 | 10/2015 | Scott et al. | |
| 2015/0306347 A1 | 10/2015 | Yagi | |
| 2016/0001040 A1 | 1/2016 | Yamaguchi et al. | |
| 2016/0030704 A1 | 2/2016 | Nishigishi | |
| 2016/0021077 A1 | 5/2016 | Ingalls et al. | |
| 2016/0296731 A1 | 10/2016 | Merk et al. | |
| 2017/0000973 A1 | 1/2017 | Otake et al. | |
| 2017/0043119 A1 | 2/2017 | Kubo et al. | |
| 2017/0072163 A1 | 3/2017 | Lim et al. | |
| 2018/0015248 A1 | 1/2018 | Logan et al. | |
| 2018/0015254 A1 * | 1/2018 | Cragg | A61M 25/0108 |

FOREIGN PATENT DOCUMENTS

| | | |
|---|---|---|
| EP | 1270031 A1 | 1/2003 |
| EP | 2572749 A3 | 3/2013 |
| JP | H09-506541 A | 6/1997 |
| JP | H10-263088 A | 10/1998 |
| JP | 2013-162979 A | 8/2013 |
| JP | 2014-508564 A | 4/2014 |
| WO | WO 93/15784 A1 | 8/1993 |
| WO | WO 1994019039 A1 | 9/1994 |
| WO | WO 2015/099935 A1 | 7/2015 |

* cited by examiner

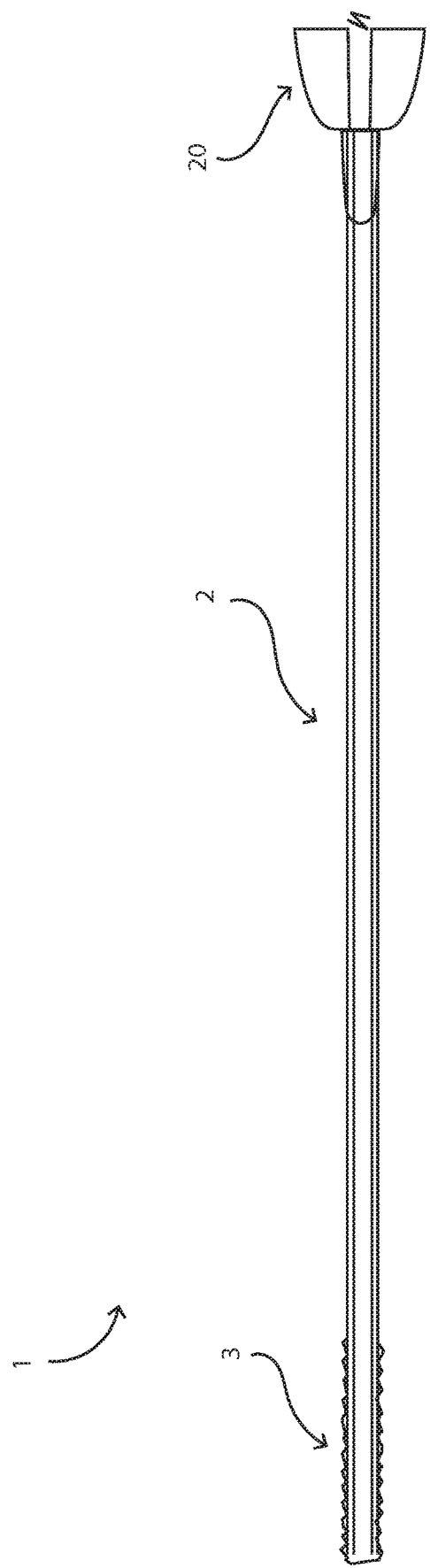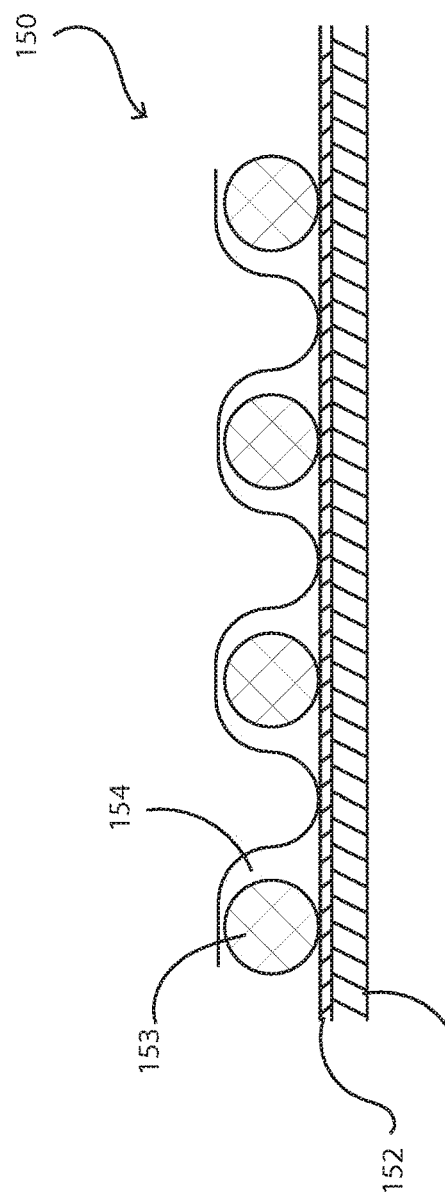

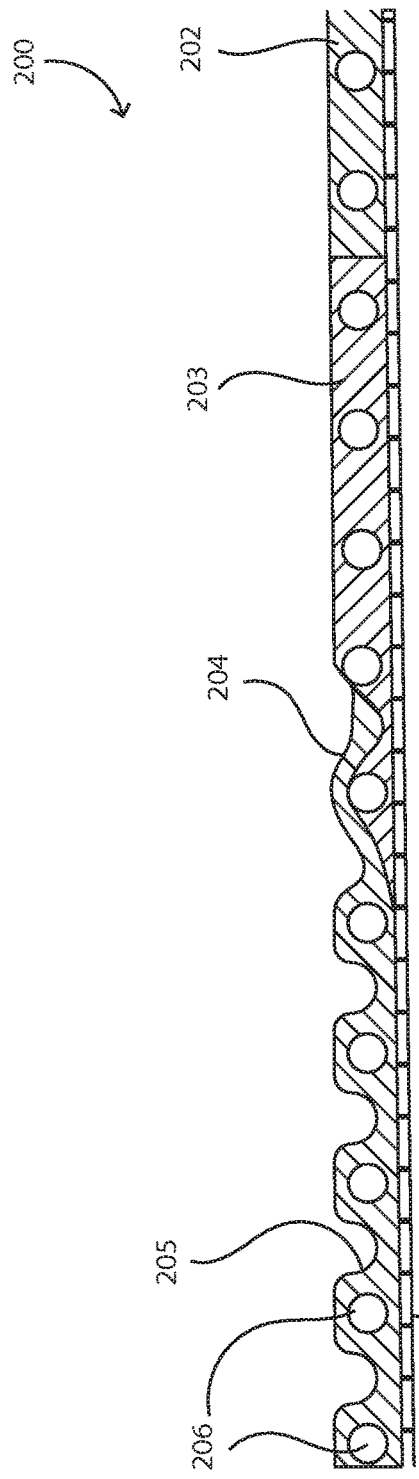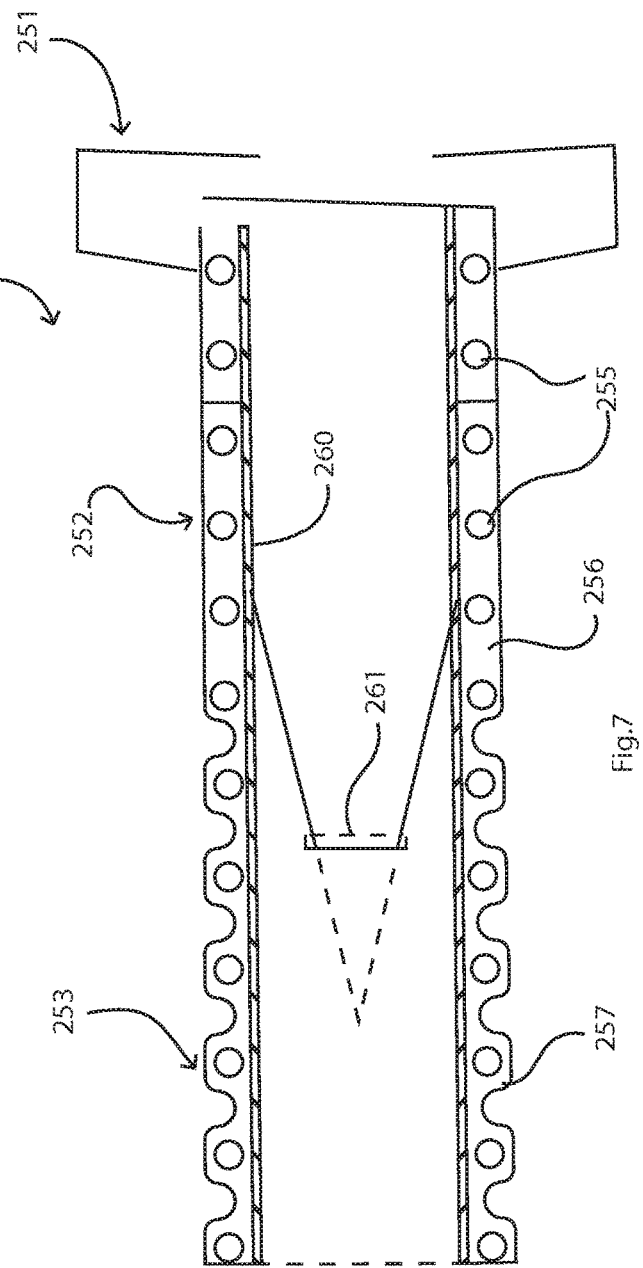

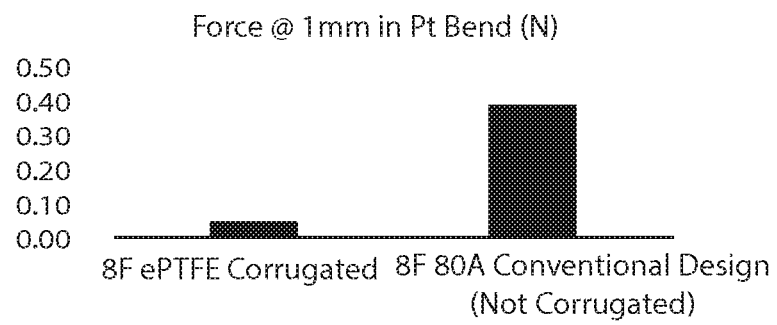
Fig.8
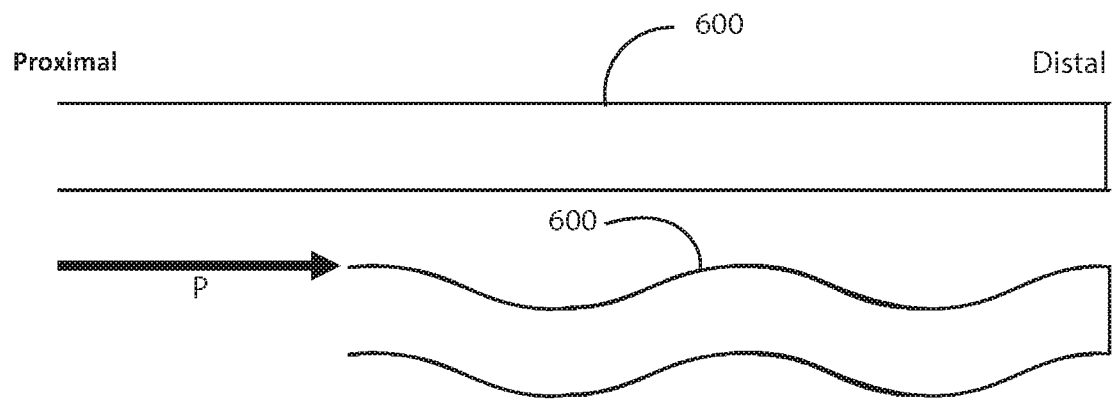
Fig.9
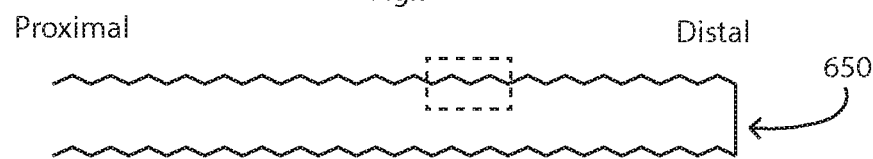
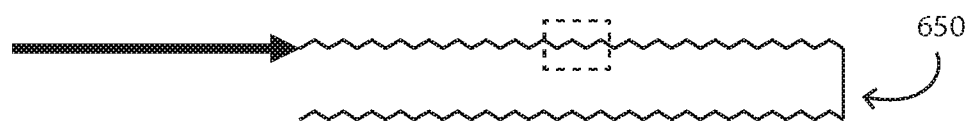
Fig.10

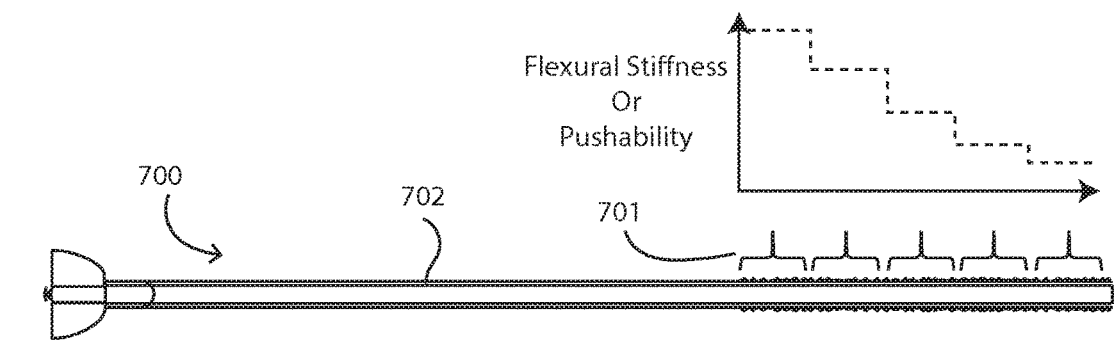
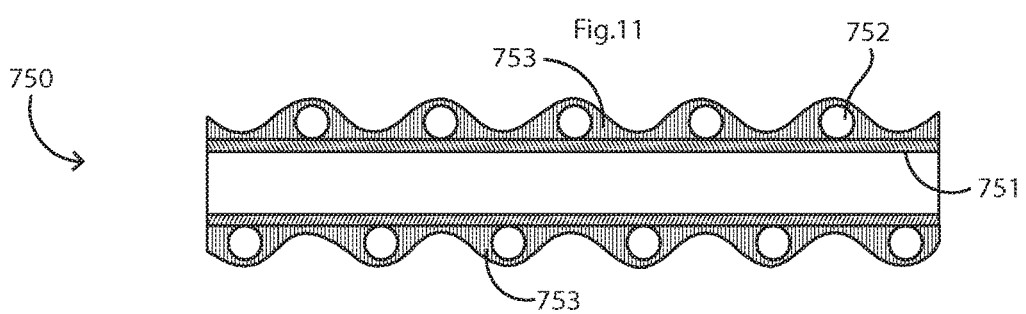
Fig.11
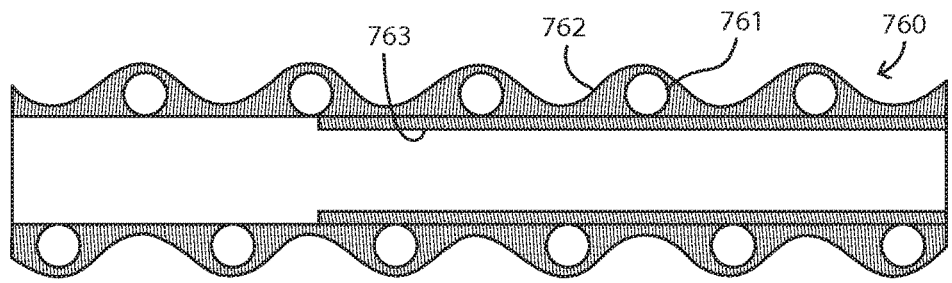
Fig.12
Fig.13
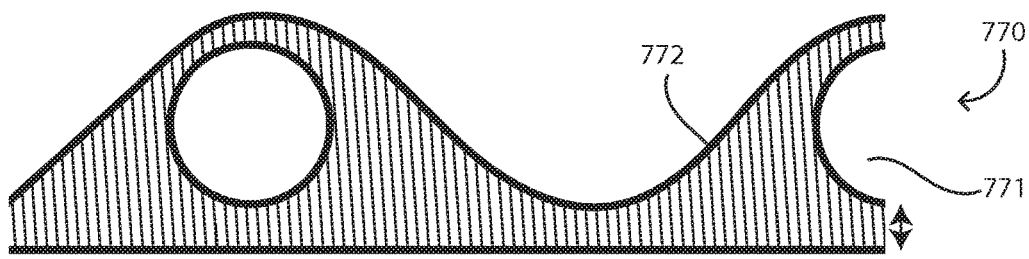
Fig.14
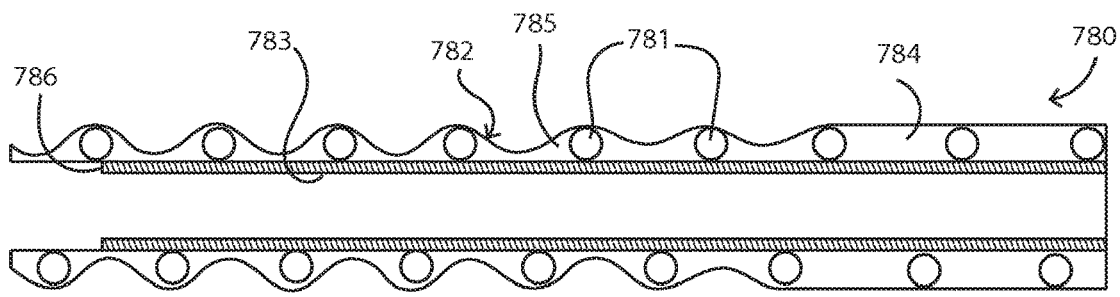
Fig.15

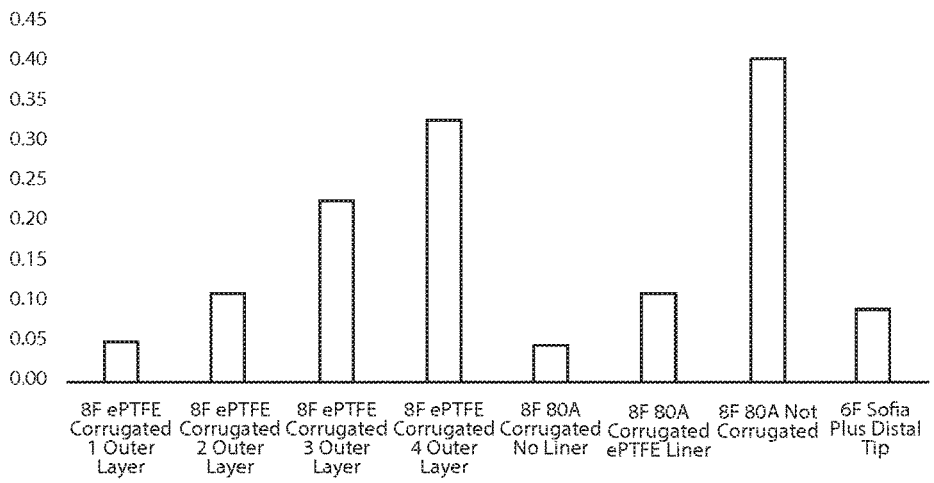
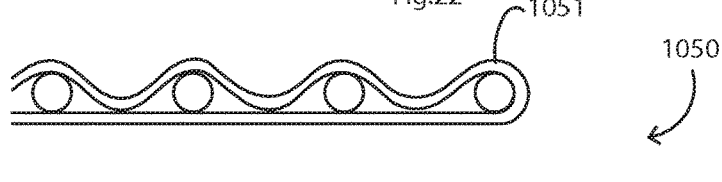
Fig.22
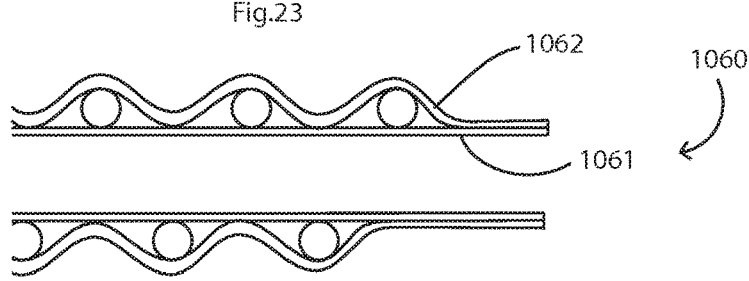
Fig.23
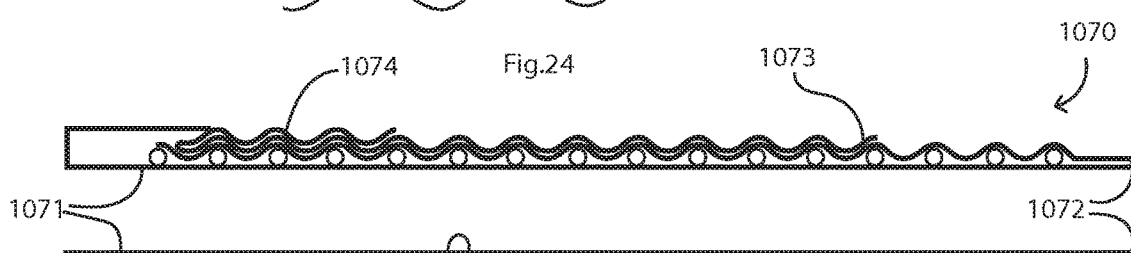
Fig.24
Fig.25(a)
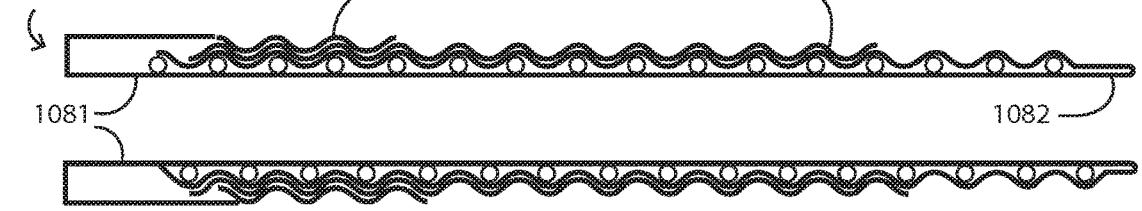
Fig.25(b)

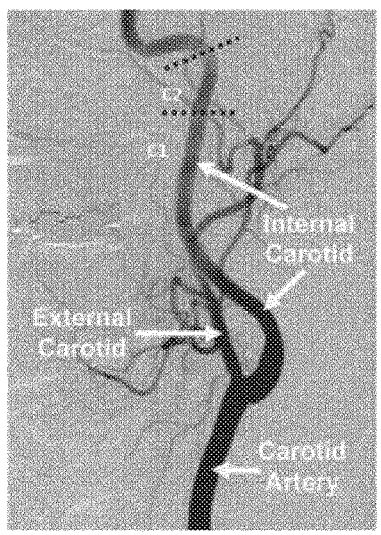
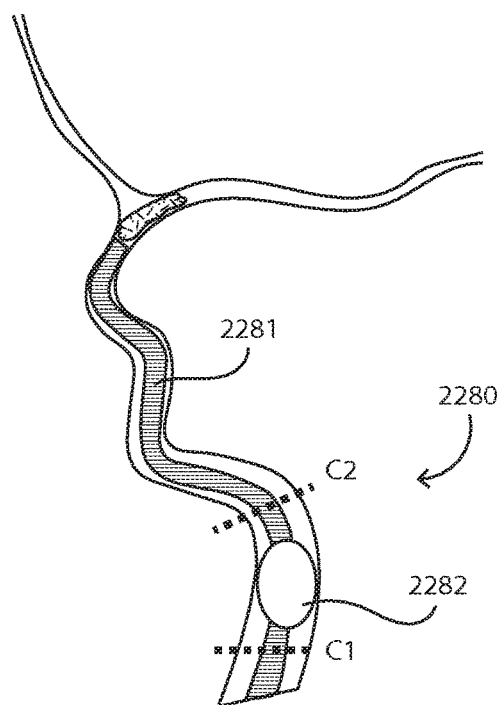
Fig.37
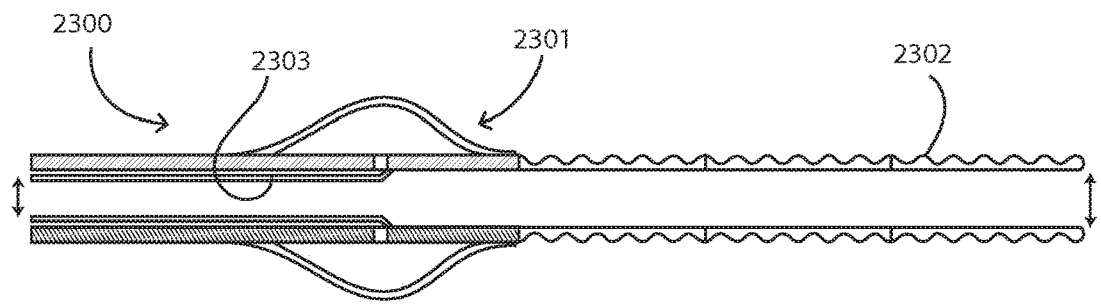
Fig.38
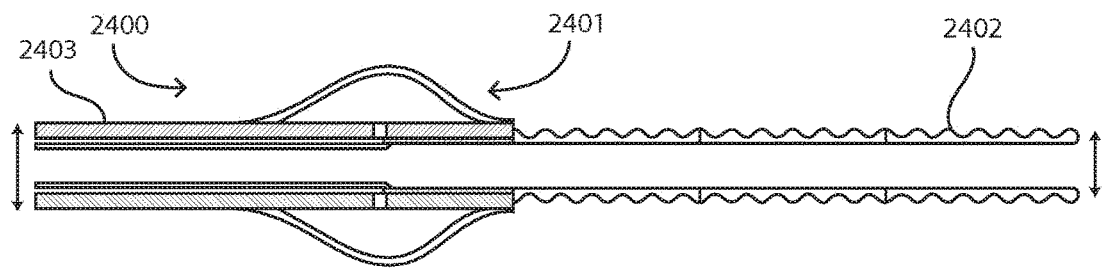
Fig.39
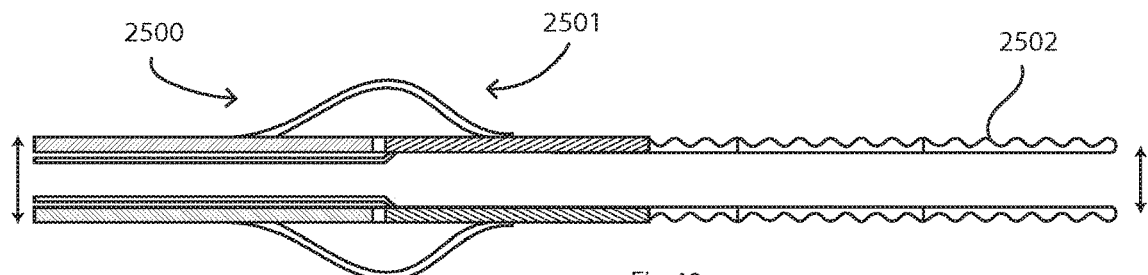
Fig.40

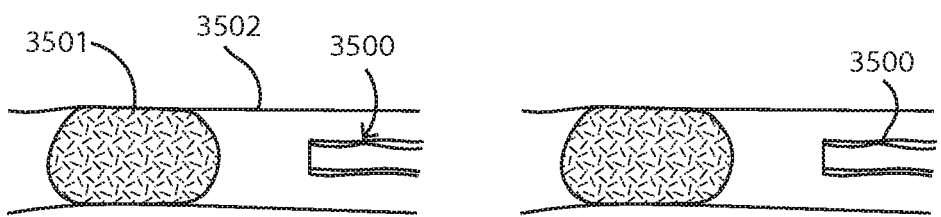
Fig.44(a)
Fig.44(b)
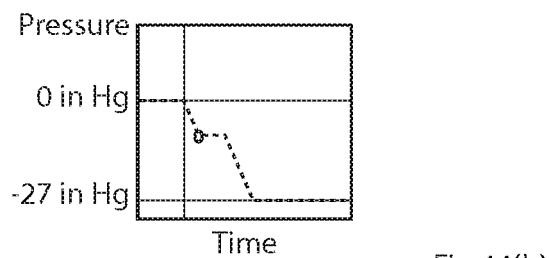
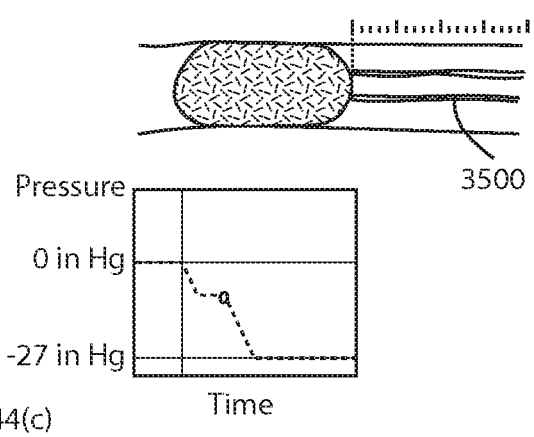
Fig.44(c)
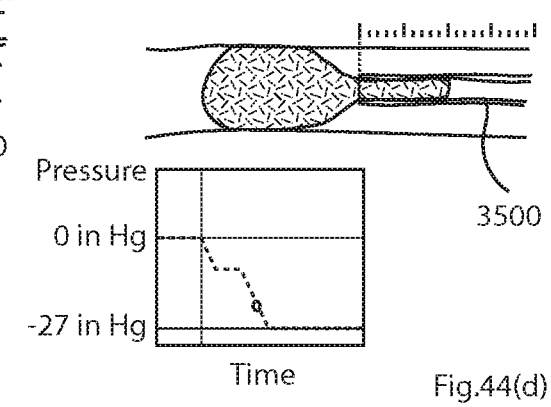
Fig.44(d)
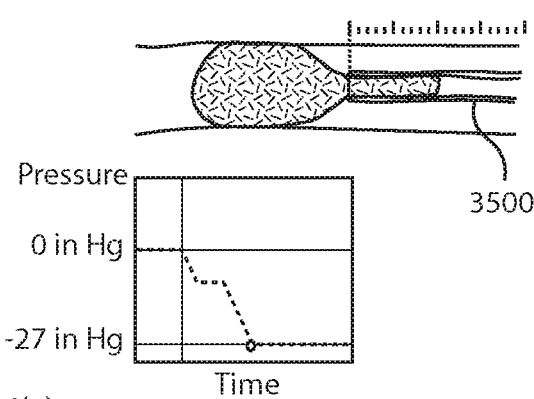
Fig.44(e)

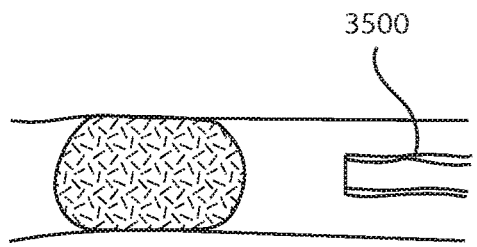
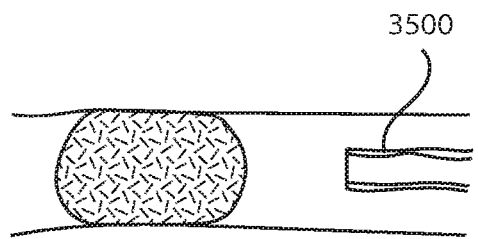
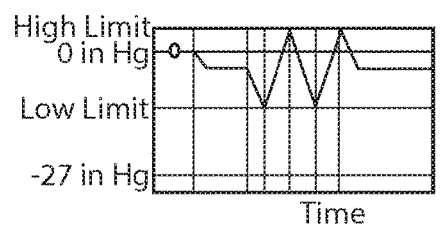
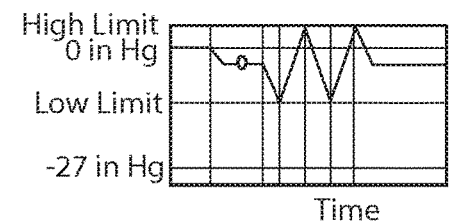
Fig.47(a)
Fig.47(b)
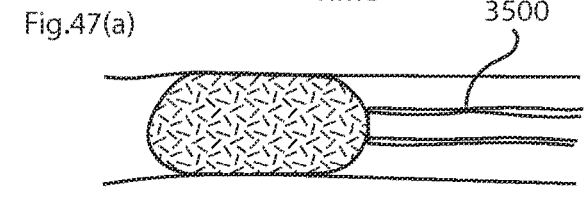
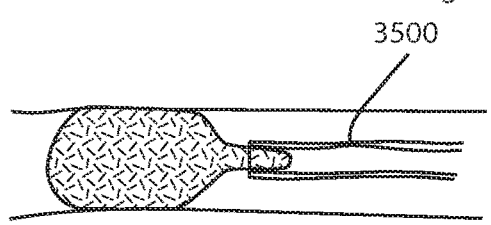
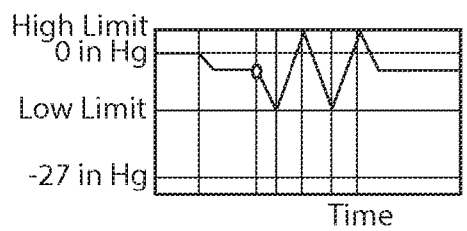
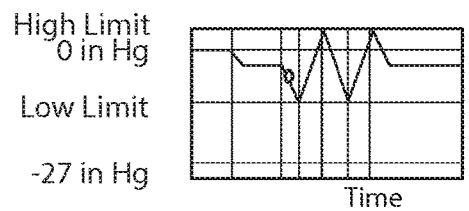
Fig.47(c)
Fig.47(d)

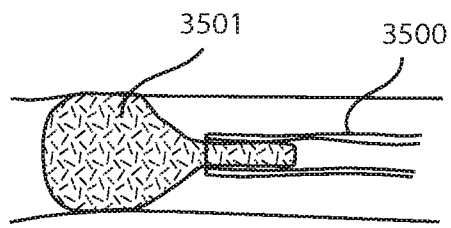
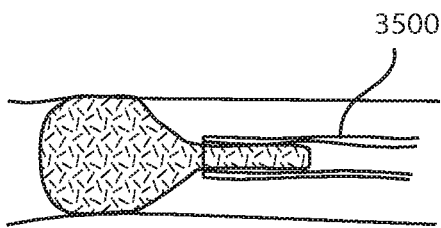
Fig.47(e)　　　　　　　　　　　　　　　　Fig.47(f)
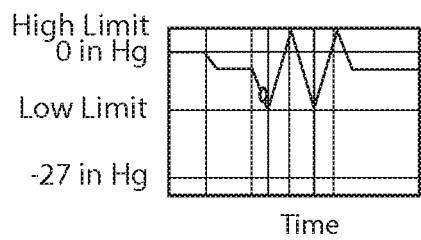
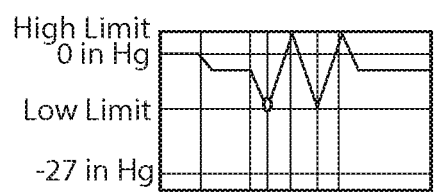
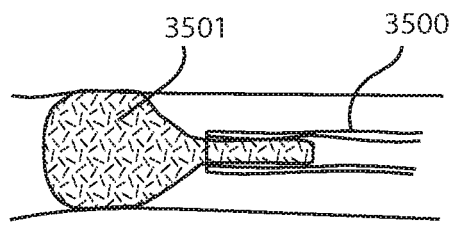
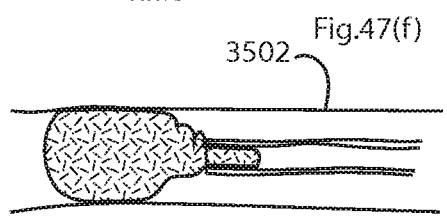
Fig.47(g)　　　　　　　　　　　　　　　　Fig.47(h)
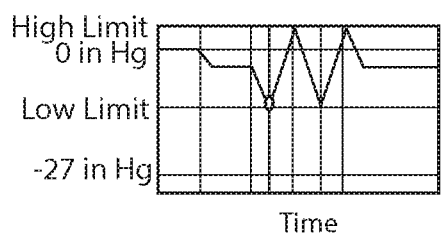
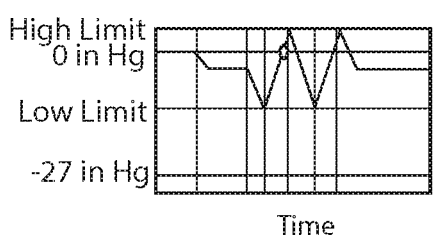
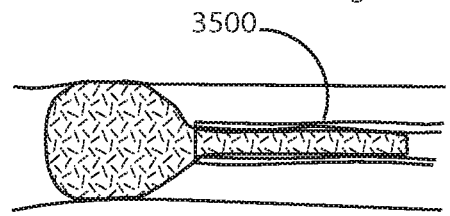
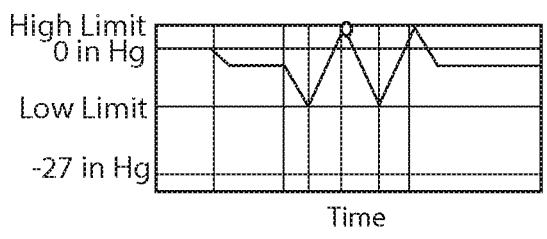
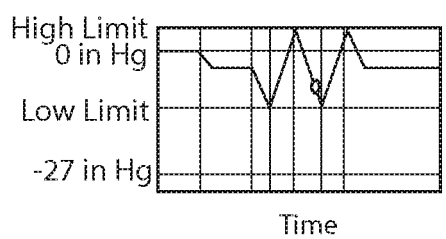
Fig.47(i)　　　　　　　　　　　　　　　　Fig.47(j)

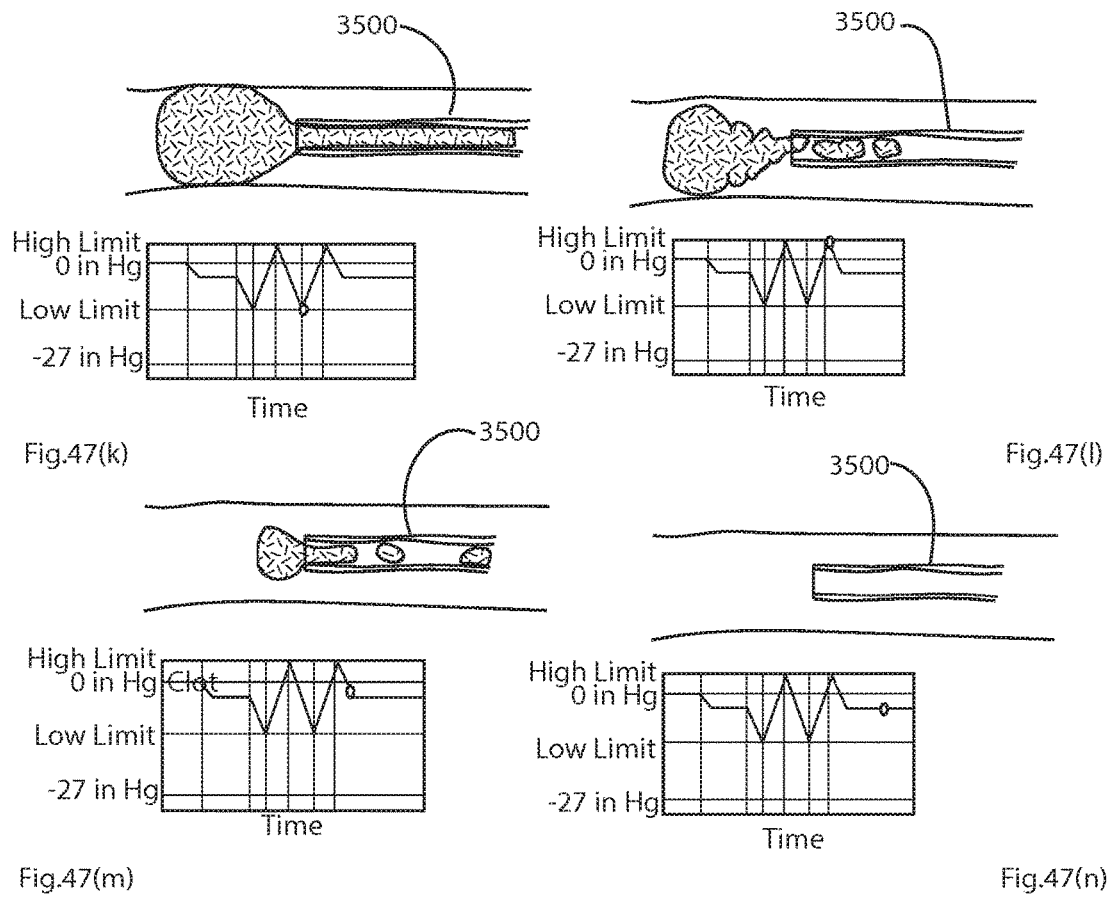
Fig.47(k)  Fig.47(l)
Fig.47(m)  Fig.47(n)
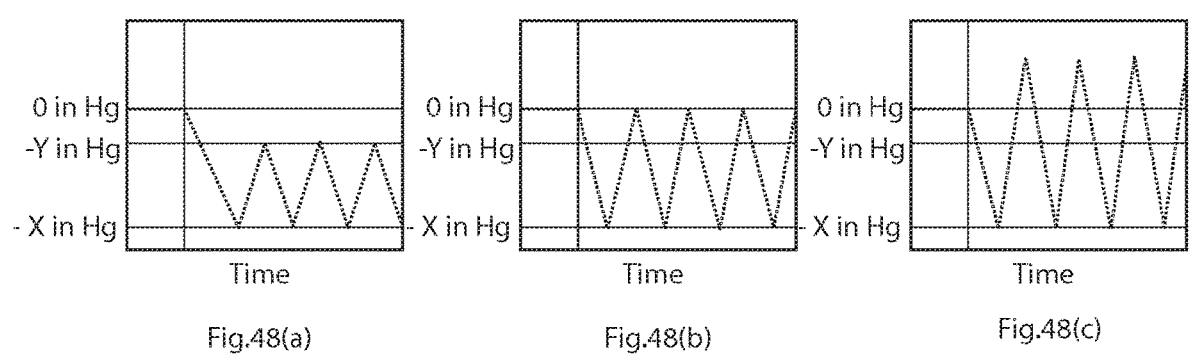
Fig.48(a)  Fig.48(b)  Fig.48(c)

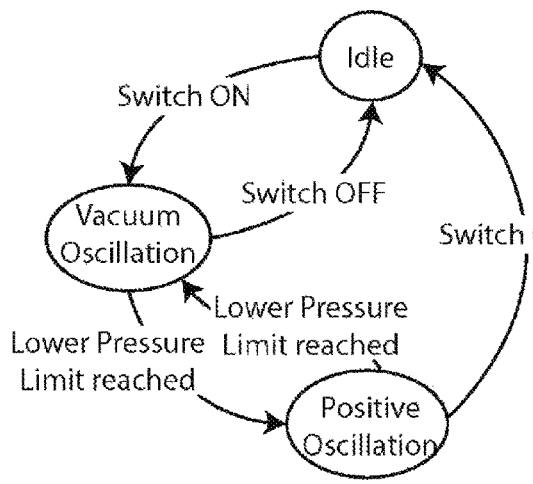
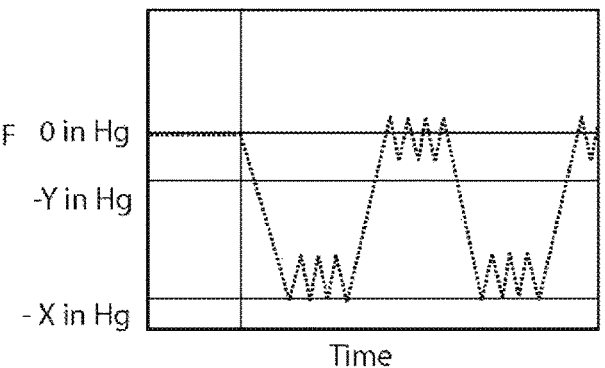
FIG. 51(a)  FIG. 51(b)
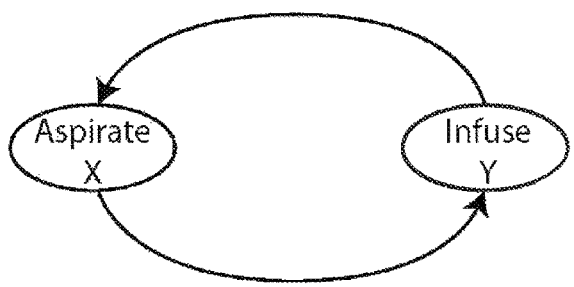
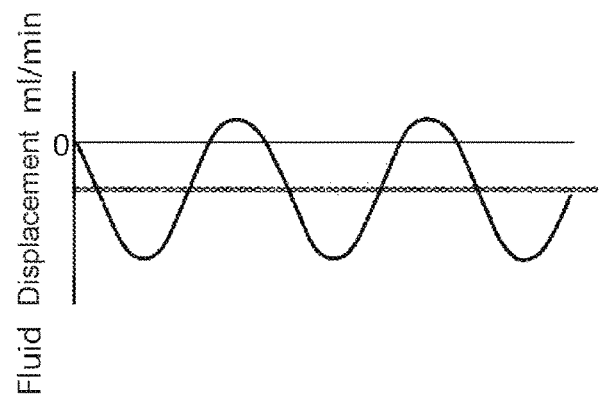
FIG. 52(a)  FIG. 52(b)
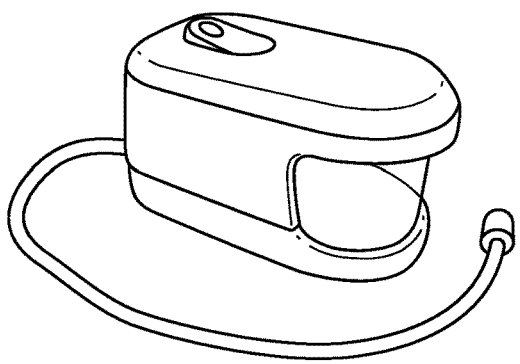
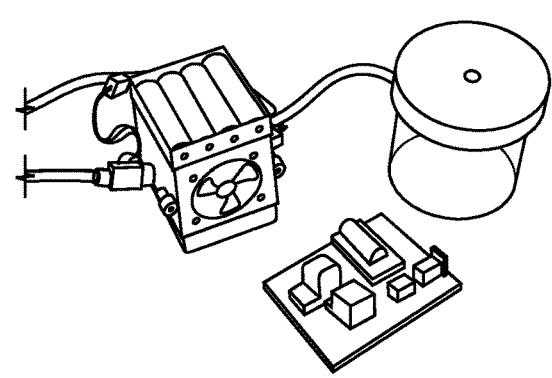
FIG. 53(a)  FIG. 53(b)

CATHETERS AND DEVICES AND SYSTEMS INCORPORATING SUCH CATHETERS

CROSS-REFERENCE TO RELATED APPLICATIONS

This application is a continuation of International Application No. PCT/EP2018/085064, filed on Dec. 14, 2018, which claims priority to U.S. Provisional Patent Application No. 62/616,188, filed Jan. 11, 2018, U.S. Provisional Patent Application No. 62/599,560 filed Dec. 15, 2017, and U.S. Provisional Patent Application No. 62/599,573, filed Dec. 15, 2017, the contents of each of which is incorporated herein by reference in its entirety.

INTRODUCTION

Field of the Invention

The present disclosure relates to catheters and to devices and systems incorporating such catheters, and to their methods of use. An example is a flexible catheter for endovascular procedures.

Prior Art Discussion

Most endovascular procedures require the use of flexible catheters, for example, to deliver contrast injection, to deliver implantable devices, perform vascular procedures, or to aspirate. Due to the tortuous nature of the vasculature, it is important for catheters to be flexible enough to travel through vessels without excessive force. However, there is generally a trade-off between the features of catheter diameter, trackability, flexibility, and kink resistance. An increase in catheter diameter tends to increase its stiffness, which lowers its trackability and may dangerously increase vascular sheer forces. An increase in flexibility tends to increase the tendency of the catheter to kink as it is pushed through the vasculature, which limits the catheter to vessels with gentle curves. In general, a decrease in wall thickness increases flexibility and allows access to more tortuous vessels, there being a trade-off between flexural stiffness and kink resistance.

The invention is directed towards providing a catheter with improved properties for desired flexural stiffness and flexibility, to thereby allow use in difficult locations such as where there are significant curves and small dimensions in the patient vessels.

SUMMARY OF THE INVENTION

A catheter has a jacket defining a lumen and a helical support. The catheter has a proximal portion and a distal portion the distal portion having for at least some of its length a corrugated outer surface. A transition portion has a flexural stiffness which is less than that of the distal portion and more than that of the proximal portion. The transition portion provides an optimum transition in flexural stiffness by way of features of the jacket including geometry of jacket corrugations, or overlapping tubular layers. The distal end of the distal portion may in some examples have an extension of liner material folded over to provide a particularly soft tip. In other examples the liner is terminated before the distal tip. The catheter is particularly suited to an aspiration device with a flow restrictor and the distal portion distal of the flow restrictor. An aspiration system may employ the catheter with a pump which dynamically applies negative or positive pressure to optimally aspirate a clot.

In one aspect we describe a catheter comprising a jacket defining a lumen and comprising a helical support in jacket material along at least some of its length, the catheter comprising at least a proximal portion and a distal portion, said distal portion having for at least some of its length a corrugated outer surface. The catheter preferably comprises a transition portion between said proximal portion and said distal portion, said transition portion having a flexural stiffness which is less than that of the distal portion and more than that of the proximal portion. The transition portion preferably has a corrugated outer surface in which at least some corrugations of the corrugated outer surface have a smaller depth and/or width than corrugations of the surface of the distal portion.

Other aspects of the catheter are set out in claims 4 to 88 of International Application No. PCT/EP2018085064.

We also describe a method of manufacturing a catheter of any embodiment, wherein the jacket is formed in at least some regions by positioning a membrane over a helical structure, applying heat so that the membrane reflows such that it forms around the helical structure, winding a tensioned cinch wire around the outside of the membrane such that it forces membrane material into grooves between each loop of the helical structure, heat setting the membrane to fix the corrugations in place, and unwinding the tensioned cinch wire leaving the corrugations behind.

The jacket may include fluoropolymers and said fluoropolymers may be bonded with each other and/or with other polymers at bonding interfaces. Chemical treatment may be applied at said interfaces using an etching solution. The etched fluoropolymer may be coated with a thin layer of urethane such as Chornoflex, and on the application of heat, this layer flows and acts to tie the fluoropolymer to a second etched fluoropolymer layer or to a different polymer layer.

In one aspect, the method comprises providing the helical support within a polymer jacket which is bonded to a liner to form a base assembly, placing an outer liner which will not bond to the polymer jacket over the jacketed coil, winding the cinch wire in a helix onto the outside of the outer liner under tension thereby imparting a corrugate geometry, heating to reflow or anneal the material to set said material into the corrugate geometry, cooling the assembly, removing the cinch wire, and peeling off the outer liner.

We also describe an aspiration device comprising a catheter of any embodiment described herein and a flow restrictor, in which the distal portion is distal of the flow restrictor. The catheter may comprise a transition portion between said proximal portion and said distal portion, said transition portion having a flexural stiffness which is less than that of the distal portion and more than that of the proximal portion, and at least part of said transition portion extends distally of the flow restrictor.

The flow restrictor may comprise a balloon and the balloon is arranged to inflate to block blood flow before aspiration of a clot into the catheter distal portion. Alternatively it may be used to block blood flow before precise delivery of an embolic agent to region of the vasculature, tumour, or organ.

Length of the distal portion is in one case suited to reach specific anatomical locations, such as the distal internal carotid artery, terminus of the internal carotid artery, proximal MI, distal MI, proximal M2, distal M2, basilar, or vertebral vessels, wherein the flow restrictor remains in or proximal of the C1 segment of the ICA.

Various aspects of the aspiration device are set out in claims 94 to 110 of International Application No.PCT/EP2018085064.

We also describe a method of use of an aspiration device of any embodiment, the method comprising steps of deploying the aspiration device in a patient's blood vessel, navigating the distal portion to a clot in the vessel, causing the flow restrictor to block blood flow, applying a vacuum to the catheter so that the clot is aspirated into the distal portion.

In one example, the method comprises:
performing an angiogram to determine location of an occlusion, and distance between petrous or cavernous carotid and the occlusion,
choosing a catheter with a distal portion length suitable to reach a clot causing the occlusion, while ensuring that the flow restrictor does not land beyond the cervical carotid,
navigating the distal portion of the catheter to the clot,
activating the flow restrictor such that flow arrest is enabled, and alternative flow pathways which could reduce the effectiveness of the aspiration are minimised,
applying a vacuum to the lumen of the catheter to aspirate the clot,
if the clot is retrieved, performing another angiogram through the balloon guide catheter or a diagnostic catheter, and
removing the catheter.

We also describe an aspiration system comprising a catheter of any embodiment, a pump linked with the catheter proximal portion, and a controller arranged to vary aspiration pressure during aspiration of a clot. The system may comprise a lumen pressure senor and the controller is configured to vary aspiration pressure according to sensed pressure within the catheter lumen. The system may comprise a lumen fluid flow sensor, and the controller is configured to vary aspiration pressure according to sensed fluid displacement in the lumen.

The controller may be configured to improve the efficiency of aspiration by preventing clogging of the catheter, and/or to promote maceration and deformation of a clot to enable it to travel through the lumen.

Various aspects of the aspiration system are set out in claims 113 to 135 of International Application No. PCT/EP2018085064.

We also describe methods of use of an aspiration system of any embodiment, in which the controller varies aspiration pressure during aspiration of a clot. There may be a lumen pressure senor and the controller varies aspiration pressure according to sensed pressure within the catheter lumen. There may be a lumen fluid flow sensor, and the controller varies aspiration pressure according to sensed fluid displacement in the lumen. Preferably, the controller improves efficiency of aspiration by preventing clogging of the catheter, and/or promotes maceration and deformation of a clot to enable it to travel through the lumen. Also, the controller may provide a vacuum or a positive pressure based on measured pressure, and change direction hence altering the pressure and fluid displacement.

The controller may have defined upper and lower limits of pressure or displacement to decide whether to apply a vacuum or pressurize, and/or it may cause the catheter to cyclically ingest and if required expel, at least some of a clot, whereby there is deformation of the clot to improve efficiency of aspiration and prevent clogging of the catheter. The controller may begin to draw some vacuum so that a negative pressure is measured and in the absence of an occlusion or partial occlusion of the catheter tip, this will be a nominal reading, representing free-flow of fluid through the catheter, and once the catheter is advanced and engaged with the clot, an increase in the vacuum is observed.

The controller may increase a vacuum to ingest more of a clot and reverse at a low limit of pressure defined such that during vacuum, a portion of the clot has been aspirated but not so much that the clot has become irreversibly clogged and the lower limit of vacuum can be set above a full vacuum pressure to prevent ingestion of too large a clot that could clog the catheter.

Other aspects of the method of operation of the aspiration system are set out in claims 113 to 135 of International Application No. PCT/EP201805064. For example, the controller may set the low limit between −100 mm-HG and −200 mm-Hg, preferably between −200 mm-HG and −300 mm-Hg, more preferably between −400 mm-HG and −500 mm-Hg, and more preferably between −600 mm-HG and −700 mm-Hg, and it may cause direction of fluid displacement of the pump to be reversed thereby increasing the pressure measured, and unloading a clot.

Detailed Description of the Invention

BRIEF DESCRIPTION OF THE DRAWINGS

The invention will be more clearly understood from the following description of some embodiments thereof, given by way of example only with reference to the accompanying drawings in which:

FIG. 4 is a cross-sectional view of the full catheter shown in FIG. 1;

FIG. 5 is a schematic cross-sectional view of a catheter wall portion having an outer tubular layer bonded with an inner tubular layer;

FIG. 6 is a schematic cross-sectional view of a transition between a distal wall portion and a proximal wall portion;

FIG. 7 is a schematic cross-sectional view of another transition between a distal wall portion and a proximal wall portion;

FIG. 8 shows force measured at a 1 mm displacement in a 3-point bend test of a conventional catheter design (0.80 A urethane jacket over a 0.005 in NiTi coil over on a 0.001 in PTFE Liner), and highly flexible corrugated ePTFE design;

FIG. 9 shows behaviour of a conventional catheter under compression when pushed against restriction, and FIG. 10 shows behaviour of a corrugated catheter under compression when pushed against a restriction;

FIG. 11 shows in a catheter use of progressively more flexible (or less "pushable") sections of catheter wall within the distal tip, distally of a proximal portion;

FIG. 12 is a section through an outer wall having a corrugated surface, with an inner liner;

FIG. 13 shows a section through a catheter in which the inner liner terminates before the of the catheter FIG. 14 shows a cross section of the catheter where the helical support is not exposed to the inner lumen of the catheter.

FIG. 15 show further constructional details of catheter walls to achieve desired flexibility at the proximal and distal portions;

FIG. 7 shows steps for manufacture of a corrugated polymer jacketed catheter section;

FIG. 22 is a plot showing results of 3-point bend tests to evaluate stiffness;

FIG. 23 shows the distal-most end of the distal portion finished by inverting an inner liner over the helical support to form a continuous element; in this instance the coil may be floating or constrained in the jacket material;

FIG. 24 shows a distal portion in which softness is improved by extending inner and outer tubular layers beyond the last coil of the helical support; in this instance the coil may be floating or constrained in the jacket material;

FIGS. 25A and 25B show further examples of catheter arrangements in which an inner liner is inverted to return as a continuous element; in this instance the coil may be floating or constrained in the jacket material;

FIG. 37 left image shows an Angiogram demonstrating the external carotid, common carotid and internal carotid artery (ICA), including the C1 and C2 segments, and right image shows acceptable positioning of the balloon;

FIG. 38 shows the proximal and distal shaft having the same outer diameter, and the proximal shaft having two concentric lumens, in which the central lumen diameter is less than that of the flexible distal tip;

FIG. 39 shows a catheter with a balloon and a distal portion having a smaller outer diameter than the proximal portion;

FIG. 40 shows a catheter with a non-corrugated proximal region of the distal section;

FIGS. 44(a) to 44(e) are schematic diagrams outlining relationship between pressure in the catheter lumen, and the clot behaviour, during aspiration;

FIGS. 47(a) to 47(n) are diagrams illustrating operation of the clot removal device in various examples;

FIGS. 48(a) to 48(c) show varying pressure signals between two vacuum levels;

FIGS. 51 (a) and 51(b) are a flow diagram and an associated plot for vacuum and positive oscillation;

FIGS. 52(a) and 52(b) are a flow diagram and an associated plot for positive and negative modulation of aspiration; and FIGS. 53(a) and 53(b) are images of a pump and its components, including a housing, a connecting tube, an on-off switch, a battery pack, a pulsatile pump, and a motherboard, in which the pressure sensor is connected to the tube (or "lumen"), which is connected to the catheter, thereby enabling pressure measurement within the catheter.

DESCRIPTION OF THE EMBODIMENTS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

Terminology

"Jacket" is the wall of the catheter, and these terms are interchangeable. It may be corrugated in all or some regions along the length (longitudinal direction). It may include any or all of a helical support (or "coil") surrounded by jacket material, and an inner liner. The inner liner, where present, defines the lumen, but otherwise the other jacket material defines the lumen. A liner where present, may be terminated at some location in the catheter.

"Tubular layer" is a layer of material of the jacket.

"Pushability" is understood as the transfer of force and/or displacement applied at a proximal portion of a catheter, along a length of the catheter, to a more distal portion of the catheter. The higher the flexural stiffness the greater the pushability.

"Corrugate" is a rib and recess geometry on the outer surface of the catheter, most often in a spiral pattern.

"Distal" means further from a clinician in use, closer to a catheter tip in the longitudinal direction, and "proximal" means closer to the clinician.

DESCRIPTION OF THE EMBODIMENTS

Figure 1:
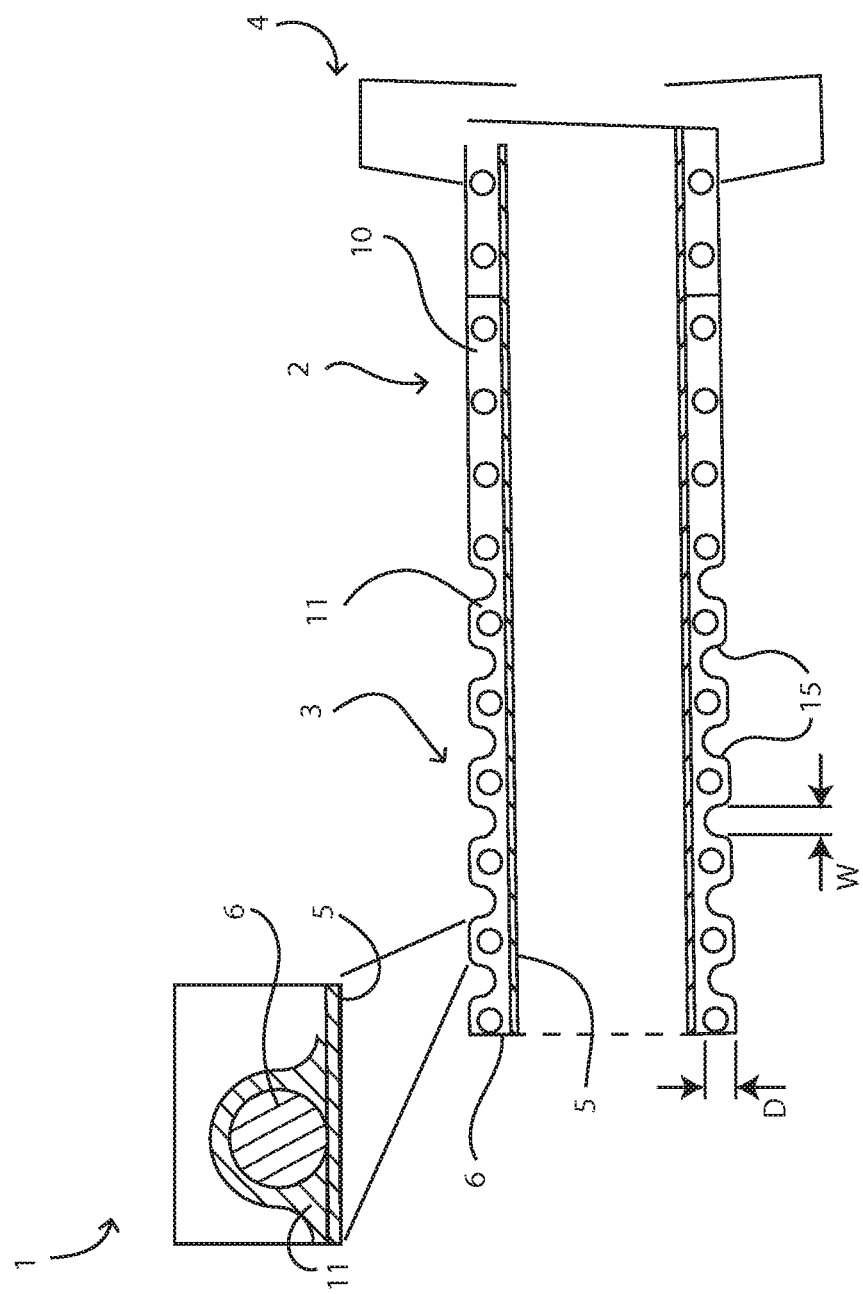
FIG. 1 is a schematic cross-sectional view of a distal end of a catheter.

FIG. 1 illustrates an embodiment of a highly flexible, kink resistant catheter 1. The catheter 1 includes a distal portion 3, a proximal portion 2, a central lumen 5 and a reinforcing structure such as a helical support 6 that runs the length of the catheter. The proximal portion and/or a transition between the distal portion and the proximal portion can in various embodiments include any of the corresponding features of the catheters described in U.S. application Ser. No. 15/647,763, filed Jul. 12, 2017, titled "HIGH FLEXIBILITY, JUNK RESISTANT CATHETER SHAFT," which is attached in the Appendix. The inner tubular layer and/or the outer tubular layer can include PTFE, ePTFE, electrospun PTFE, silicone, latex, TecoThane, nylon, PET, Carbothane (Bionate), SIBS, Tecoflex, Pellethane, PGLA, or Kynar, Polyethylene and cyclic olefin copolymers, PEEK.

The inner and outer tubular layers (FIG. 1) in at least the distal portion can be formed from a single section of material or a number different sections of similar or different material. In this embodiment the outer tubular layer 11 of the distal portion is formed from a polyurethane (e.g. Pellethane 80AE) and the inner tubular layer 5 is formed from ePTFE and/or PTFE.

In this case the catheter jacket comprises an inner liner 5 and an outer tubular later 11 with a helical support C. The highly flexible distal portion 3 (left side) of the catheter is created by forming corrugations 15 into the outer surface of the outer tubular layer 11. The helical support 6 is encapsulated between the corrugations of the outer tubular layer 11 and the outside of the smooth inner tubular layer 5 as shown in FIG. 1. The formation of a corrugated wall structure during bending provides flexibility while reducing the likelihood of kinking. The corrugated outer surface can also decrease resistance when the outer surface of the catheter contacts a vessel wall. The depth of the corrugations may be tailored to provide a desired variation in stiffness along the length of the catheter as shown in FIG. 2.

As shown in FIG. 1 a parameter "D" is depth of a corrugation and a parameter "W" is the width of a corrugation. The width is not the distance from peak to peak, rather it is the effective width of the valley. In effect for many embodiments this is provided during manufacture by tightening a cinch wire around a tubular layer, heat treating, and removing the cinch wire to provide the corrugated surface. The width W it approximately the diameter of the cinch wire in this case. The depth D is not necessarily uniform because the pressure applied by the cinch wire may vary along the length of the catheter thereby forming deeper indentations in some locations than in others.

Figure 2:
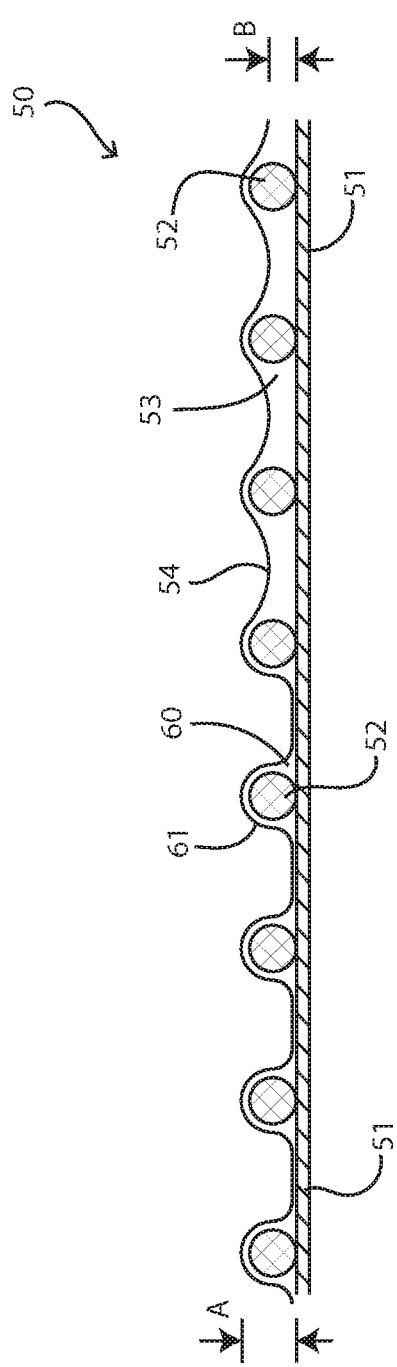
FIG. 2 is a cross-sectional view of a catheter wall portion having varying depths of corrugation.

FIG. 2 shows a cross section through a wall of a catheter tip 50, having an inner layer 51, a helical coil support structure 52, an outer layer 53 with a corrugated surface 53. The depth A of the corrugations on the left hand side is greater than the depth B on the right hand side. The section with the lower corrugation depth B may function as a transition region before a tip (left hand side) with more flexibility.

Figure 3:
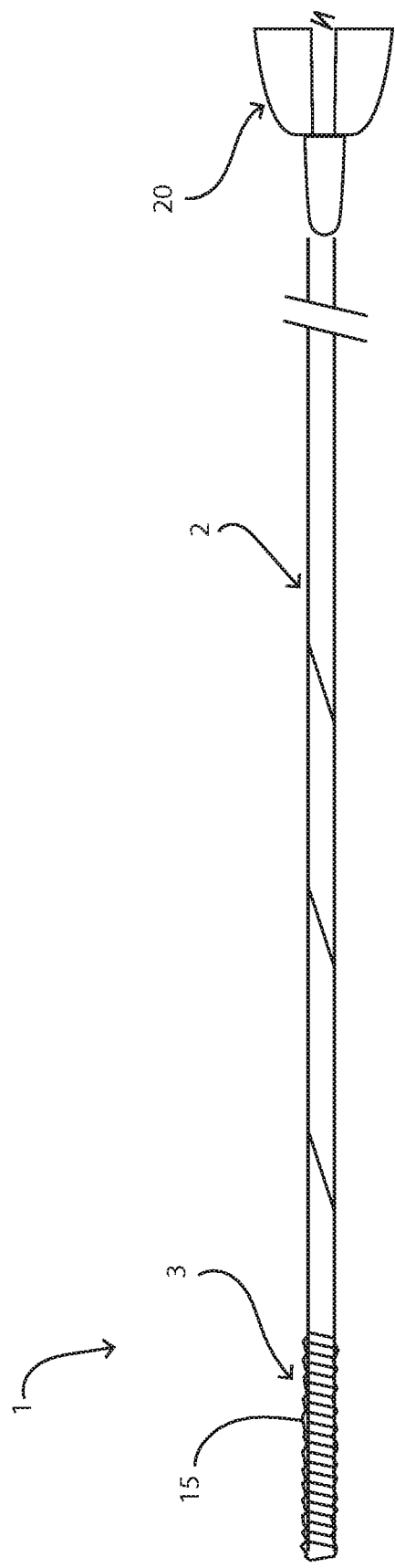
FIG. 3 illustrates an outer surface of the catheter shown in FIG. 1.

In the examples of FIGS. 1 and 3 the coil is embedded in the jacket; being constrained from movement relative to the surrounding jacket material.

Additionally, pitch, or corrugation width variations may be used to control the flexibility locally in the corrugated region. Also, flexibility may be set during manufacture by choosing some length of the coil to be embedded in the jacket or to be floating, the region with the floating coil being more flexible. Where the coil is floating it is in the context of the jacket tubular layers being attached in the spaces between corrugation rubs, such as a jacket tubular layer to an inner liner.

The outer tubular layer can extend at least a length of the highly flexible distal portion or extend beyond the distal portion for some distance along the proximal (midsection) length or extend the entire length of the catheter as shown in FIGS. 3 and 4 (which shows the catheter of FIG. 1 in its full length). Extending the outer tubular layer at least some length beyond the highly flexible distal portion of the catheter allows for a controlled stiffness transition between the distal and proximal portions of the catheter and for the formation of a robust joint between the outer tubular layer and any additional outer jacket materials. Again, flexibility may be set during manufacture by choosing some length of the coil to be embedded in the jacket or to be floating, as is the case for any of the embodiments described with reference to FIG. 3 or 4.

To form the corrugations in a tubular membrane, the membrane can first be positioned over the helical reinforcing structure. On the application of heat, the outer tubular membrane will reflow such that it forms around the helical structure. A tensioned wire can then be wound around the outside of the tubular membrane such that it forces portions of the membrane into the grooves between each loop of the supporting helical structure. The tubular membrane can then be heat set to fix the corrugations in place. After this process the tensioned wire may be unwound leaving eh corrugations behind.

The inner tubular layer can extend into the proximal portion of the catheter to provide an uninterrupted lumen and to join or improve the joint strength between the highly flexible distal portion of the catheter and the proximal portion of the catheter. The diameter of the inner tubular layer can be constant (e.g. smooth surface). The inner tubular layer may form at least part of or the entirety of the liner as shown in FIG. 4. The inner tubular layer can be made from a low friction material such as ePTFE or PTFE.

As explained above, the outer tubular layer of at least the distal portion is formed from a polyurethane (e.g. Pellethane 80AE) and the inner tubular layer is formed from an ePTFE and/or PTFE liner. It is necessary to attach these layers together and this is not easily achieved as fluoropolymers do not form strong bonds with other materials.

To facilitate bonding between fluoropolymers (e.g. ePTFE and PTFE) and between fluoropolymers and other polymers such as polyurethanes (e.g. Pellethane) the outer or bonding surface of the fluoropolytner(s) may be chemically treated using a sodium-based etching solution such as FluoroEtch. The etching solution removes fluorine atoms from the surface of the fluoropolymer and prepares it for bonding.

The etched fluoropolymer can then be coated with a thin layer of urethane, such as ChronoFlex. On the application of heat, this thin ChronoFlex layer flows and acts to tie the fluoropolymer to a second etched fluoropolymer layer or to a different polymer layer as shown in FIG. 5. This embeds the coil.

This diagram shows part of the cross-section of a catheter at its distal portion 150. This includes a liner 151 of ePTFE or PTFE, a tie layer 152 of urethane or FEP tape or FEP powder. Also, there is a Nitinol™ coil 153 in an outer jacket 154 of ePTFE, or urethane material. The nitinol coil 153 is encapsulated between the outer tubular corrugated layer and the smooth inner tubular layer 151. The tie layer 151 serves the purpose of attaching the liner 151 to the outer jacket material. If the liner is of ePTFE material then it will need to be etched to strip the fluorine atoms so that it will form a better bond with the tie layer.

Again, flexibility may be set during manufacture by choosing some length of the coil to be embedded in the jacket or to be floating, as is the case for any of the embodiments described below with reference to FIGS. 6 and 7.

The ChronoFlex™ tie-layer 152 is so thin it does not cause any significant change in wall thickness. An alternative form of tie-layer involves the use of FEP. The fluoropolymer may be sputter coated with a FEP powder which under heat and pressure forms a bond between the coated fluoropolymer layer and a second layer. An ultra-thin FEP tape may also be used in the same application.

The helical support is encapsulated between the corrugations of the outer tubular layer and the smooth inner tubular layer as shown in FIG. 5. The inner tubular layer and the outer tubular layer are bonded together in the space between the adjacent loops of the helical support by such mechanisms as a tie-layer. The helical support is bonded within the helical channel formed by the corrugated outer tubular layer, i.e., the helical support is molecularly or physically attached to the outer tubular layer. The helical support may also be bonded to the outside surface of the smooth inner tubular layer. The distal portion of the catheter retains highly flexibility and kink resistance because of the advantages inherent in a corrugated outer structure and using materials of appropriate stiffness and thickness.

In the present configuration, the pitch of the helical support may vary over the length of the catheter to influence the flexural stiffness of the catheter. For example, the helical support could have a different pitch at the proximal loops compared to the distal loops.

If the outer tubular layer of the distal portion of the catheter is formed from a fluoropolymer such as ePTFE or PTFE and the outer tubular layer of the proximal portion is formed from a different polymer then achieving a good bond, especially one that resists delamination during tracking, can be difficult. This may be overcome by sandwiching the outer layer of the proximal portion of the catheter between the inner and outer tubular layers of the distal portion of the catheter as shown in FIG. 6.

FIG. 6 shows a portion 200 of a catheter, having an inner lumen 201 with a liner, an outer layer 203 of Pellethane 80AE material, and Nitinol coils 206. On the right hand sider the catheter has a smooth outer surface 203, and distally in a transition section there are corrugations 204 with a small depth, and more distally deeper corrugations 205 for more flexibility. The arrangement of having a transition section between proximal and distal sections may be referred to as a "sandwich arrangement".

If the inner tubular layer of the distal portion of the catheter is formed from a different material or different section of material from that of the inner tubular layer of the proximal portion then the tubular layers can be joined by creating a small slit or window in one tubular layer and pulling a spliced length of the other tubular layer through it as shown in FIG. 7. The helical support is then wound around the outside of these layers thus keeping them together.

FIG. 7 shows a catheter section 250 with a proximal end 251, a transition section 252, and a distal tip 253, and a spliced proximal layer 260 with a window 261.

In various embodiments the helical support is physically attached by being constrained or embedded in the catheter wall to move with its surrounding wall material. Such embedding might be achieved at an interface between the coil and solely the jacket material, or combination of an interface of the jacket material and the inner liner.

The embedding can be achieved by a very tight fit between the coil and the surrounding material. Generally, there is no gap between the surrounding wall material and the coil. Due to the three-dimensional geometry of the coil, when within a surrounding material, it is unable to move independently.

Due to the manufacturing technique in which the material may be moulded around the coil, there is no play between the coil and jacket, meaning it cannot move independently. That is to say, the coil is immovable without concurrent movement or deformation the surrounding jacket material.

This lack of play, and tightness of fit means there is an interfacial friction between the coil and surrounding material, further providing constraint, and meaning the coil and surrounding material must move together.

In other embodiments, the coil may be floating, that is to say there is not a tight fit between the material in the jacket and the helical coil. In these instances, there is some play between the helical support and the jacket. This is particularly the case where the jacket material surrounding the helical support is comprised of ePTFE. In this instance, even in the presence of a relatively tight geometric fit, the material is quite supple and may allow movement of the helical support relative to the ePTFE.

In general, the following are some preferred parameter ranges for aspects of the catheter.

For at least some of the length of the catheter the width of the corrugate is no more than 50% of the pitch of the corrugate.

For at least some of the length of the catheter the width of the corrugate is between 5% and 49% of the pitch of the corrugate, and more preferably the width of the corrugate is between 15% and 45% of the pitch of the corrugate.

For at least some of the length of the catheter the width of the corrugate is between 20% and 45% of the pitch of corrugate.

For at least some of the length of the catheter the width of the corrugate is at least 10% of the jacket thickness.

For at least some of the length of the catheter the width of the corrugate is at least 20% of the jacket thickness.

At the most distal region of the distal portion the width of the corrugate it at least 60% of the jacket thickness.

At the most distal region of the distal portion the width of the corrugate it at leak 60% of the wall thickness and the depth of the corrugate is at least 70% of the wall thickness.

The ratio of the width of the corrugate to the depth of the corrugate is at least 0.5 in at least one region of the catheter In the embodiments described below the coil may be either embedded or floating in some or all regions of the catheter, unless stated otherwise.

Referring again to the construction of the catheter structure, we achieve a catheter with a highly flexible distal tip, to ensure that a smooth transition in flexural stiffness and pushability is achieved between the flexible distal portion and the proximal portion of the catheter, which may be of more conventional construction. A smooth transition prevents areas of stress and strain concentration within the catheter shaft. Such areas have potential for kinking of the catheter, delamination of layers of material, and/or of damage to key bonds within the catheter.

Bench testing demonstrates the large difference between the stiffness of a conventional catheter tip design and a highly flexible corrugated design. Smoothly bridging of this gap presents a technical challenge.

FIG. 8 shows force measured at a 1 mm displacement in a 3-point bend test of a conventional catheter design (0.80 A urethane jacket over a 0.005 in NiTi coil 0.018 in (0.45 mm) pitch over on a 0.001 in (0.025 mm) PTFE Liner), and highly flexible corrugated ePTFE design (inner and outer 0.002 in (0.05 mm) wall ePTFE 0.9 g/cm$^3$ density, with a 0.005 in (0.125 mm) NiTi coil, 0.018 in (0.45 mm) pitch.

It should be appreciated that while very good catheter shaft flexibility allows the catheter to navigate extremely tortuous bends at low force and reduced potential for vessel damage, it can also lead to some compromise in pushability. For clarity, pushability is understood as the transfer of force and/or displacement applied at a proximal portion of a catheter, across a length of the catheter, to a more distal portion.

Catheter flexibility may limit the transfer of a displacement applied at a proximal portion of the catheter to a distal portion of the catheter. This implies a portion of the displacement is absorbed through global deformation of the catheter as shown in FIG. 9. FIG. 9 shows behaviour of a conventional catheter under compression when pushed against restriction. In this instance the length of the catheter 600 has not changed. In general, it is this type of shortening which occurs in catheters of conventional construction.

FIG. 10 shows behaviour of a corrugated catheter 650 under compression when pushed against restriction. In the case of a corrugated outer jacket with a thin inner and outer tubular layer, the deformation may be accommodated by the catheter wall. The inner and or outer tubular layers of the catheter can deform locally, particularly in the recess meaning the overall length is reduced. Some of the global deformation of the catheter as shown in FIG. 9 would also be expected.

This soft compressive behaviour is advantageous at the distal tip as the catheter tip is limited in its ability to move forward causing vessel damage or dissection. However, in cases in which the distal tip is very long, some increased pushability in the proximal portion of the tip may be preferable to allow the physician to navigate the catheter distally and proximally as intended.

In one configuration one or more regions of varying pushability and flexibility are present within the catheter tip comprised of one or more of the regions of a rib and recess construction. FIG. 11 shows in a catheter 700 use of progressively more flexible or less pushable sections of catheter wall 701 within the distal tip, distally of a proximal portion 702. In one configuration the most flexible region is on the distal tip of the catheter.

These regions of increased/decreased pushability/flexural stiffness are achieved by a number of features such as embedding of the helical support, alterations to the inner and outer tubular layers (wherein the helical support may or may not be floating between the inner and outer tubular layers), or the use of an in-fill material.

The change in the stiffness or pushability via the transition region may be gradual change or via multiple steps. Where it is stepped or gradually changed it may be achieved by having a particular tubular layer terminated, or by a change to the degree of corrugation or a change in material.

It is envisaged that any or all of these approaches may combined on some or all of the catheter shaft. Examples are as follows:

A distal tip in which at least some is of corrugated material which embeds a helical support, wherein the degree of corrugation is altered progressively proximally to achieve in increase in stiffness. The most distal region may or may not have a liner. The liner is ePTFE, transitioning to PTFE in a more proximal region. The most proximal portion may not be corrugated.

A distal tip in which at least some is comprised of a floating coil between ePTFE layers with a corrugated design, wherein the thickness of the ePTFE material increases progressively, or in steps proximally. This may be achieved by increasing the wall layer thickness, or by the addition of layers material. The ePTFE liner transitions to PTFE in a more proximal region. The most proximal portion may not be corrugated.

A distal region may be comprised of a floating coil between ePTFE layers of corrugate design and more proximally a corrugated embedded portion, and more proximally again of an un-corrugated portion. The ePTFE liner transitions to PTFE in a more proximal region. A distal corrugated region may be combined with a more proximal corrugated region with increasing wall thickness, or the addition of a layer of material to the wall to increase stiffness. The most proximal portion may not be corrugated.

In one configuration the helical support is embedded by being bonded to the outer jacket, of for example ePTFE material. This has the effect of stiffening the catheter wall construction, when compared to a floating helical support, thus reducing the flexibility and increasing the pushability.

In one configuration, in a catheter portion 750 the helical support 752 is embedded in a matrix 753 of continuous porous flexible material such as ePTFE. The outer wall has corrugated surface, as shown in FIG. 12. An inner tubular layer, or liner 751, as shown in FIG. 12, may not be required.

While ePTFE provides a very soft flexible material in the catheter construction it is also compressible due to its porosity. Furthermore, when used as a thin tubular layer which deforms easily locally, macro pushability can be compromised if an area of the catheter becomes impeded particularly if the distal tip meets a resistance. To improve pushability while maintaining high flexibility, an incompressible flexible material may be used for embedding instead of a porous material such as ePTFE. This means it can accommodate deformation more readily than materials which are not porous.

The corrugations allow localised deformation, while a region of continuous incompressible material ensures the efficient transfer of axial force and displacement along the length of the catheter. By reducing the depth of the corrugations, and correspondingly increasing the thickness of the continuous material, the pushability of the catheter can be increased, while the flexibility is reduced. This may be described as a corrugated jacket design.

In one embodiment the inner tubular layer is comprised of ePTFE. In one configuration the helical support is transposed from the inner liner such that it is not exposed to the liner. This is to prevent movement or debonding of the helical support, and to prevent it placing local stress or strain on the liner of the catheter. The corrugation geometry may be of semi-circular, U-shaped groove, V-shaped, or square groove.

In one configuration the width of the corrugate at the surface of the catheter is at least 5% of the wall thickness of the wall. Preferably, in at least one section the width of the corrugate at the surface of the catheter is at least 10% of the wall thickness at the wall. Preferably, in at least one region of the distal tip, the width of the corrugate at the surface of the catheter is at least 30% of the wall thickness at the wall.

In one embodiment the corrugate depth is between 5% and 95% of the catheter wall thickness. In one configuration the corrugate depth is at least 20% of the catheter wall thickness in at least one section of the catheter.

In one embodiment, the corrugate depth varies along the corrugated region of the catheter from a larger depth distally to smaller depth proximally. In one embodiment, the corrugate width varies along the corrugated region of the catheter from a larger depth distally to smaller depth proximally. In another embodiment, the corrugate depth varies from a larger depth distally to smaller depth proximally, while the width is substantially constant along the length of the corrugated section of the catheter.

In one embodiment the corrugate represents the impression of a circular helical wire wound from a depth and width of no impression, i.e. no corrugate, to a depth of at least 50% of the wall thickness. It should be appreciated in that instance that the width of the corrugate is varying from 0 to a maximum width equivalent to the diameter of the helical wire, or impression which remains following removal of the helical wire.

It should be appreciated that a tensile force on the wound cinch helical wire is required to create the corrugations. For example, a 0.005 in 304 Stainless Steel circular cross section wire at 1N tension wound at a force 1N, on an 0.006 in wall thickness 80 A jacket with an ID of 0.088 in will achieve a 10-20% depth of corrugation. Increasing the tension to 1N tension wound at a force 7N will achieve a 40-70% depth of corrugation. Varying levels of force will induce different degrees of corrugation. It should be appreciated that corrugations of high depth D as shown in FIG. 1 will allow the catheter section to flex at a relatively low force. This is because the global bending of the catheter is actually concentrated within the recess of the corrugate.

However, if the corrugation has a very low width, even very deep and numerous corrugations will have a limit to the degree of bending the catheter can accommodate. This is because adjacent corrugations will start to touch one another. Therefore, the flexural stiffness will be low until the adjacent corrugations contact one another, or "bottom-out", at which point the flexure stiffness will increase. Bending will then be accommodated by deformation of the rest of the catheter wall (and no longer primarily within the recesses)

This bottoming-out means the catheter shaft has a lower limit of bend-radius which it can achieve via deformation within the recess. Further bending deformation beyond the bottoming-out limit is achievable but is not accommodated by deformation at the recess of the corrugation; it is accommodated by pressing adjacent corrugations against one another. This is generally at a very high force compared to the deformation which occurs at lower bend radii while the deformation is focused in the recess.

The width of the corrugate should be controlled so as to be large enough to accommodate sufficient deformation within the recess to reach the desired lower limit of bend-radius at relatively low force of bending. This is important as physicians generally wish to be able to navigate catheters at low forces so that the potential for vessel damage is reduced, and the catheters are not deforming the vessels in order to travel forward.

While the width and depth of the corrugation contribute to the flexural stiffness of the catheter, the width can dominate the lower limit of bend-radius to which the catheter can deform. Accordingly a larger corrugate width enables a lower bend radius at a low force of bending.

Consider the example of an 0.088 in ID (2.2 mm/catheter with a wall thickness of 0.006 in (0.15 mm) with an 0.005 in (0.125 mm) diameter Nitinol helical support of 0.018 in pitch embedded in 80 A, over an ePTFE Liner. A sample with a 0.004 in (0.1 min) corrugate width and 0.006 in corrugate depth will yield a force in 3 pt bending of 0.05N at 1 mm deflection, and a bottom out bend radius of 5 mm. A sample with a 0.007 in (0.175) corrugate width and 0.006 in corrugate depth will yield a similar force in 3 pt bending but bottom out bend radius of 3.5 mm.

In order to allow a large catheter to enter the cerebral vessels safely, and to accommodate lower radii bends such as those of the carotid siphon, the width of the corrugate should be of a minimum value relative to the pitch and or wall thickness.

In one embodiment the width of the corrugate is no more than 50% of the pitch of the corrugate (same as the pitch of the helical support). Preferably the width of the corrugate is between 5% and 49% of the pitch of the corrugate. More preferably the width of the corrugate is between 15% and 45% of the corrugate. More preferably the width of the corrugate is between 20% and 45% of the corrugate.

In one embodiment the width of the corrugate is at least 10% of the wall thickness. Preferably the width of the corrugate is at least 20% of the wall thickness. In one embodiment at the most distal section of the tip the width of the corrugate it at least 60% of the wall thickness.

In one embodiment at the most distal section of the tip the width of the corrugate it at least 60% of the wall thickness and the depth of the corrugate is at least 70% of the wall thickness.

In another embodiment the corrugate represents the impression of a circular helical wire wound from a depth and width of no impression, i.e. no corrugate, to a depth of at least 70% of the wall thickness.

In one configuration, the inner tubular layer (liner) terminates in a region proximal to the distal end of the catheter. This will further reduce the stiffness of the catheter for a corrugated or uncorrugated configuration. In this instance, particularly in the case wherein the catheter wall is comprised of a material such as a silicone, urethane or pebax, the region without a liner may be tacky. In one embodiment the region of inner lumen of the catheter without a liner has hydrophilic or hydrophobic coating to improve lubricity. This is shown in FIG. 13 for a catheter portion 760 having a helical support 761 embedded in an outer jacket 762, and in which an inner liner 763 extends for part of this length but terminates before the distal end (left side).

In one embodiment the un-lined section is at least 1 cm in length, preferably at least 2 cm in length. The termination of the liner is advantageous in allowing a more flexible section of the catheter. However, this can also form a sudden change in flexural stiffness and potential location for kinking or high stress or strain. This may be managed using a change in corrugation parameters, or by skiving the liner. In another embodiment, the termination of the liner is a skive, or angular cut.

In one configuration a section of the un-lined jacket material adjacent to the liner proximally is less corrugated than the section of unlined jacket distally and proximally. This may be achieved by decreasing the depth of the corrugation. In another configuration a corrugated section of the lined jacket adjacent to the unlined jacket has a longer pitch than the section of unlined jacket distally and proximally.

In one configuration the helical support is transposed from the inner liner such that it is not exposed to the inner lumen of the catheter as shown in FIG. 14, having a helical support 771 in an outer jacket 772. This is to prevent pop-out the helical support into the catheter lumen during bend of the catheter. In one embodiment the distance from the inner lumen to the helical support is at least 0.005 mm.

Referring to FIG. 15, in a catheter portion 780 there is a helical support 781, and an outer jacket 782 and an inner liner 783. The outer jacket 783 has a proximal part 784 without corrugations, distal part 785 with corrugations. The inner liner 783 terminates proximally of the distal end at 786. This is an example of a configuration n which the most distal section of the distal tip is comprised of a corrugated jacket without a liner, a more proximal section is corrugated and contains a liner, at least one section even more proximally is more corrugated, and at least one section even more proximally again is un-corrugated. In one embodiment all sections of the jacket are of the same material durometer. In one embodiment the material is urethane of durometer 80 A. In another embodiment more proximal jackets are of a stiffer urethane or pebax are present. The liner is comprised of ePTFE. In a more proximal section of the shaft, the liner may transition to PTFE. In one embodiment this transition takes place in a more stiff durometer material than that of the jacket of the corrugated distal tip.

Figure 16:
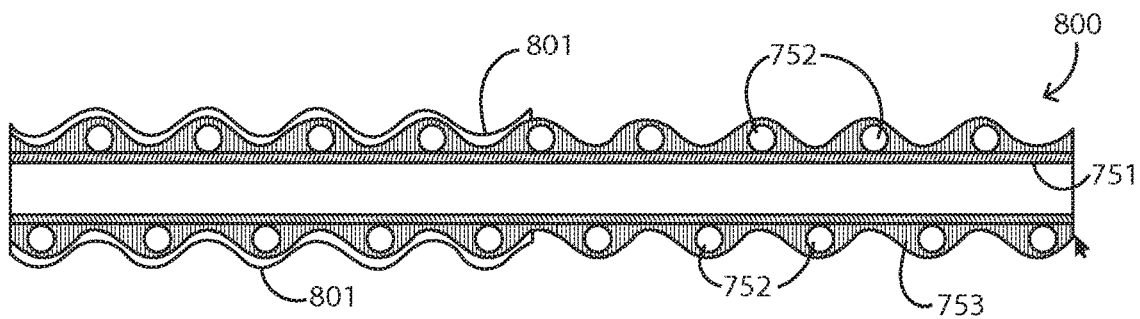
FIG. 16 shows an outer tubular layer added to the outside of the corrugated structure which embeds the helical support to further increase the stiffness of a section of the catheter proximally of the distal end.

In one embodiment, a catheter portion 800 has a liner 751, a helical support 752, and an outer jacket 753 as for the catheter portion 750. However, in this case there is an outer tubular layer 801 added to the outside of the corrugated structure which embeds the helical support to further increase the stiffness of a section of the catheter proximally of the distal end, as shown in FIG. 16. This layer may be of the same or different material as the material used to encapsulate the helical support. Materials of higher stiffness such as PET or Nylon pr PEEK or other polymer can be used in this instance without significantly adding to the profile. In one embodiment a layer of PET is added which has a thickness of 0.05 mm or less, preferably 0.025 or less, and more preferably 0.0125 mm or less.

Figure 17:
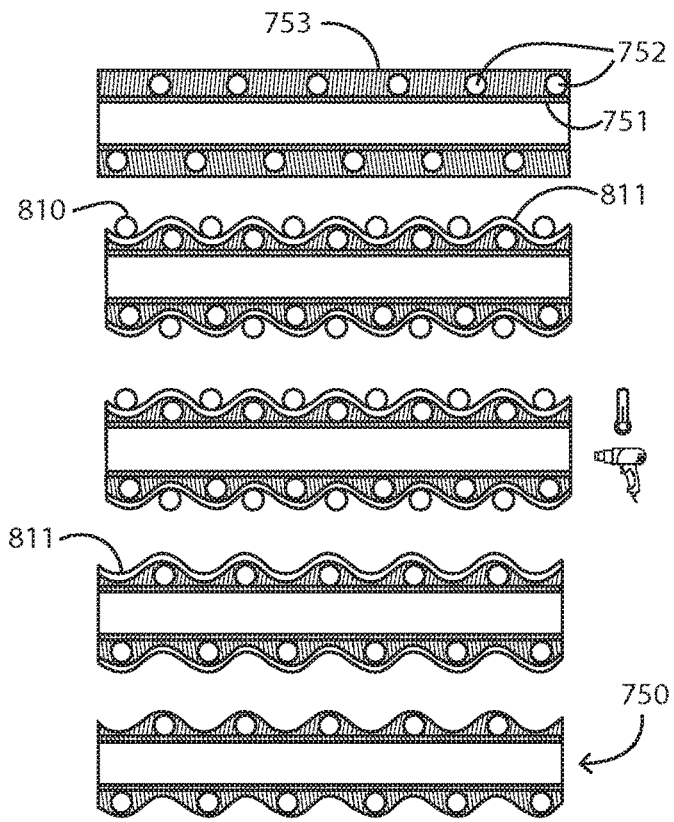

In order to manufacture a corrugated polymer jacketed catheter section a number of approaches may be taken. The following steps may be used as shown in FIG. 17:

A conventional catheter construction containing a coil 752 embedded within a polymer jacket 753 is bonded to a PTFE liner 751 is built to form a base assembly.

An outer liner 811 which will not bond to the polymer jacket is then placed over the jacketed coil. Fluoro polymers of high flexibility such as FEP or PTFE or more preferably ePTFE may be used.

A wire 810 is wound in a helix onto the outside of the outer liner under tension imparting a corrugate geometry on the construction. This may be termed a "cinch wire"

The construction is heated to reflow or anneal the material, setting it into the corrugate geometry The assembly is cooled The cinch wire 810 is removed The outer liner 811 is peeled off the assembly to complete the process.

Figure 18:
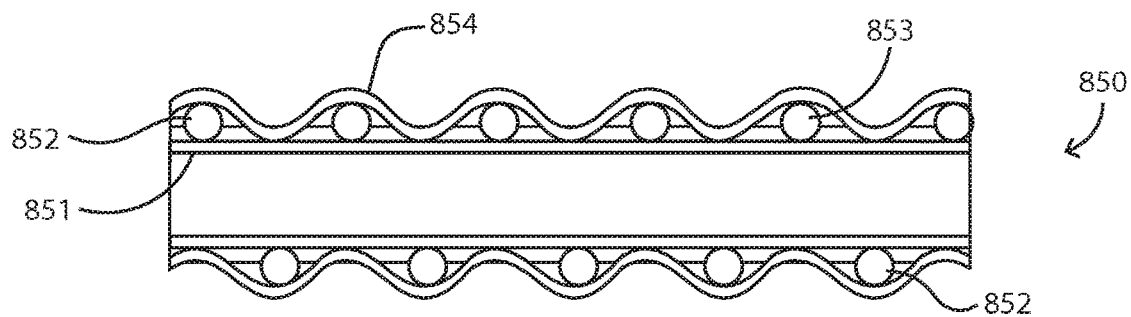
FIG. 18 shows a catheter portion with a liner, a coil and inner and outer tubular layers respectively and in-fill for increased stiffness.

An in-fill material may also be used to manage flexibility and increase pushability, and where it is used it embeds the coil. FIG. 18 shows a catheter portion 850 with a liner 851, a coil 852 and inner and outer tubular layers 853 and 854 respectively and in-fill for increased stiffness In one embodiment the material is used only to partially fill the space around the helical support as shown in FIG. 18. In another embodiment the in-fill material completely fills the helical channel around the helical support between the inner and outer tubular layers. In yet another embodiment the in-fill material is melted to form a layer of material on all surfaces within the helical channel.

In one embodiment the outer and inner tubular layer are comprised of ePTFE or PTFE, and the in-fill material is PET, PEEK or FEP The helical channel may be formed using a helically wound wire (cinch wire) placed temporarily on the outside of the outer tubular layer. To permanently form the helical channel, the construction may then be heated such that the in-fill layer melts to flow between the helical support, the outer tubular layer, and the inner tubular layer. Upon cooling and removal of the helically wound cinch wire on the outer tubular layer, the corrugate configuration is maintained, and an adhesive chemical bond is achieved between the components via the in-fill material.

In one configuration the in-fill material may be a polyurethane, pebax, PET, silicone, latex, TecoThane, Nylon, PET, Carbothane, SIBS, Tecoflex, Pellethane, PGLA or Kynar, Polyethylene and cyclic olefin copolymers, PEEK.

In one configuration the inner tubular layer and outer tubular layer of ePTFE are bonded to one another via sintering. It must be appreciated that in the case of a fluoropolymer, and in particular ePTFE or PTFE for use as the inner and outer tubular layers, the temperature required for the sintering can exceed 500° C. In this instance it may be preferable to use materials for in-fill with a high processing and degradation temperatures such as PET, FEP, or PEEK. Other materials such as urethane or pebax will degrade at lower temperature and are not suitable.

As PET is a relatively stiff material it can be introduced in small volumes to stiffen the corrugate structure without significant impact on catheter profile or completely filling of the helical channel. This may provide regions of floating and of embedded coil.

In one configuration an increase in the pushability or stiffness is achieved by changing the thickness of one or both of the tubular layers. An increase in thickness increases the intrinsic stiffness of the wall. It also means a reduction in the available space for localised material bending and deformation. Therefore, the flexibility may be reduced. Furthermore, as the thickness increases the axial cross-sectional area along the axis of transmission of force and displacement along the catheter increases.

Figure 19:
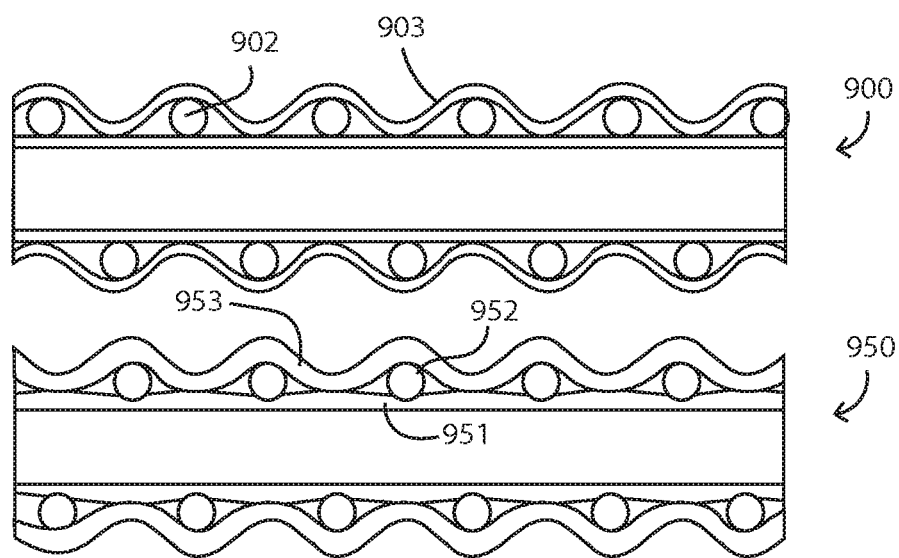
FIG. 19 shows both the inner and outer tubular layer thickness being increased; in this instance the coil may be floating or constrained between the outer layer and inner liner.

In one embodiment, both the inner and outer tubular layer thickness are increased, as shown in FIG. 19 for the catheter portion 950 as compared to the catheter portion 900. In the catheter portion 900 there is an inner liner 901, a coil 902 and an outer tubular layer 903. In the catheter portion 950 there is a thicker inner liner 951, a coil 952, and a thicker outer tubular layer 953. In another embodiment the inner tubular layer thickness alone is increased. In yet another embodiment the outer tubular layer thickness alone is increased.

Figure 20:
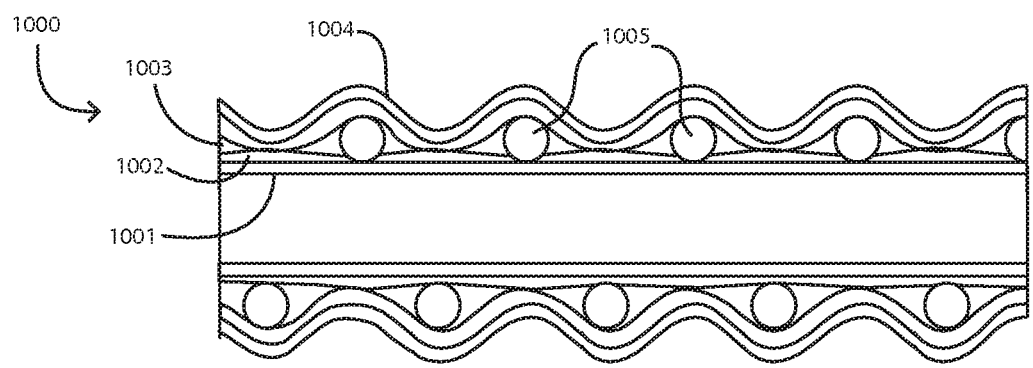
FIG. 20 shows a catheter portion having a liner, an outer jacket layer underneath a coil, and two layers outside the coil; in this instance the coil may be floating or constrained in the jacket material.

In another configuration the total outer tubular wall thickness may be altered by the addition of one or more layers of the same material. Referring to FIG. 20 a catheter portion 1000 has a liner 1001, an outer jacket layer 1002 underneath a coil 1005, and two layers 1003 and 1004 outside the coil 1005.

The total inner tubular layer wall thickness may be increased by the addition of one or more layers. These layers may be of the same or different materials. In the case of ePTFE, the combined thickness of the inner tubular layers in an unconstrained configuration may be between 0.025 mm to 0.3 mm, preferably between 0.5 mm and 0.2 mm.

In one configuration the inner and outer tubular layers are comprised of multiple layers of ePTFE, wherein there is at least one layer between an outer tubular layer and an inner tubular layer. The total thickness of (for example, ePTFE) tubular layers which are comprised of one or more layers may be between 0.025 mm to 0.3 mm, preferably between 0.05 mm and 0.2 mm. The density of the material (again, such as ePTFE) may be approximately 0.9 g/cm$^3$. Increasing or decreasing the density of the material will necessitate a bigger or smaller wall thickness to achieve the same effect.

In another embodiment the inner tubular layer thickness is constant along the length of the tip, but the outer tubular layer thickness is larger in at least one region. In another embodiment the outer tubular layer thickness is increased proximally at least once along the length of the catheter tip.

Figure 21:
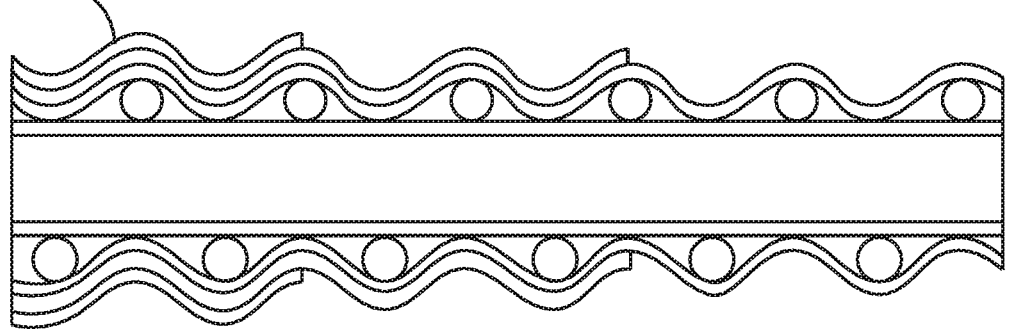
FIG. 21 shows, in order to achieve a controlled change in stiffness of the distal tip, multiple layers being overlapped to achieve a precise level of stiffness; in this instance the coil may be floating or constrained in the jacket material.

In order to achieve a controlled change in stiffness of the distal tip, multiple layers may be overlapped to achieve a precise level of stiffness as shown in FIG. 21 in which an additional outer layer 1010 is present for part of this catheter portion. This principle may be used for any number of layers, to achieve a desired variation in stiffness. Similarly, single thicker layers may be used proximally, connected to a thinner layer more distally to achieve the same effect.

In one embodiment the tip has one outer tubular layer of 0.025 mm to 0.075 mm across the length of the tip. A second additional outer tubular layer of thickness 0.025 mm to 0.075 mm is present in a region more proximally. A third additional outer tubular layer of thickness 0.025 to 0.075 mm is present in a region even more proximally. A fourth additional layer of thickness 0.025 to 0.075 mm is present in a region even more proximally.

In one embodiment the distal tip comprises an outer tubular layer of 0.05 mm across the length of the tip. A second additional outer tubular layer of thickness 0.05 mm is present in a region more proximally. A third additional outer tubular layer of thickness 0.05 mm is present in a region even more proximally. A fourth additional layer of thickness 0.05 mm is present in a region even more proximally.

In one configuration the tubular layers are bonded to one another. The bond may be present across the entire interface of the tubular layers. Alternatively, the bond may only be present at recesses of the corrugations, in the area where the inner and outer tubular layer are in contact. In yet another embodiment, the bond is present between the layers at the rib and recess regions of the corrugations. In another embodiment the material of the inner or outer tubular layer may be changed to one with a higher stiffness to increase the stiffness of the wall.

It should be noted that some variation in the thickness of the tubular layers may be present locally following bonding of inner and outer tubular layers, or their constituent layers, due to the use of local compression (pressure) to ensure a strong bond between tubular layers. This is particularly so with ePTFE because it is a porous compressible material. This localised compression may reduce the wall thickness in that area.

To evaluate a subset of the embodiments described above, 8F catheter samples of inner diameter 0.088 in were built and tested in a Three Point Bend Test. The force at a 1 mm displacement was measured using a 50N Load. Cell on a Zwick Roel tensile test machine. The distance between the supports was 20 mm. Clear changes in stiffness were achievable using the various configurations outlined above.

It can be appreciated that the embodiments described above can be used to alter the stiffness of the catheter wall as desired. For comparison, a 6F Microvention Sofia Plus catheter indicated for use in neurovasculature is included. FIG. 22 shows results of 3-point bend tests to evaluate stiffness of various embodiments described above.

In the neurovasculature, when entering delicate vessels such as M1, M2, ICA, vertebral and basilar arteries, an atraumatic tip of critical importance. It is preferable that the distal tip has a minimum length of its most flexible section such that the catheter tip will deflect or absorb deformation rather than causing vessel damage.

In one embodiment the distal and flexible sections of the catheter of corrugate rib and recess design is a minimum of 1cm in length and is comprised of inner and outer tubular layers in a corrugate configuration, with a floating helical support within a helical channel. In one embodiment for an 8F catheter distal tip, the force in 3-point bend test, for a span of 20 mm, at 1 mm deflection, should not exceed 0.1N.

As shown in FIG. 23, in one configuration, the distal-most end 1050 of the distal portion is finished by inverting an inner tubular layer 1051 over the helical support to form a continuous element.

Referring to FIG. 24, in another embodiment, in a distal end 1060 the softness of the distal tip end is improved by extending inner and outer tubular layers 1061 and 1062 beyond the last coil of the helical support.

As shown in FIG. 25A, in a distal portion 1070 an inner tubular layer 1071 is inverted at the distal end 1072 to return as a continuous element. Inner and outer tubular layer are comprised of the same piece of material and are continuous. An extension of ePTFE at the end 1072 of the corrugated section is present to improve tip softness. Preferably, an extension beyond the last coil is between 0.5 and 5.0 mm. More preferably the extension beyond the last coil is between 1.0 and 0.3 mm. The distal portion 1070 also has an outer tubular layer 1073 terminating before the distal end 1072, and a concentric further outer tubular layer 1074 around the layer 1073 for part of the length of the layer 1073. This staggered overlapping arrangement provides a transition portion with stepped changes in flexural stiffness.

FIG. 25B shows a catheter distal portion 1080 with an inner liner 1081 which extends out at the distal tip to form an extension. In this case there are also overlapping staggered outer tubular layers 1083 and 1084.

In the catheter 1070 two or more layers are achieved by using the same piece of material inverted and returned along the length or a portion of the catheter. In one instance two pieces of ePTFE are used to achieve one inner tubular layer, and three outer corrugated tubular layers.

In the catheter 1080 additional layers are added discretely. In another embodiment, a combination of inverted continuous layers and discrete layers is used. The proximal portion of the catheter (shown un-corrugated) may be corrugated or un-corrugated.

Figure 26:
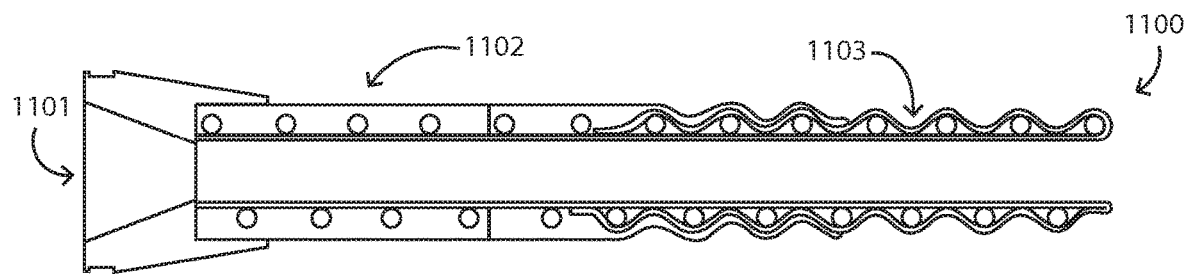
FIG. 26 shows in a catheter having a proximal end and an intermediate portion an inner tubular layer of WIFE material extending along the entire length of the catheter including a distal end, where it is bent back to be continuous.

PTFE material is a relatively stiff material compared to eTPFE and so is therefore preferable to avoid the use of PTFE as an inner tubular layer (liner) particularly in areas which will be subject to significant bending during passage through tortuous vessels. In one embodiment, as shown in FIG. 26, in a catheter 1100 having a proximal end 1101 and an intermediate portion 1102 an inner tubular layer is of ePTFE material and this extends along the entire length of the catheter including a distal end 1103, where it is bent back to be continuous with the outer tubular layer.

Figure 27:
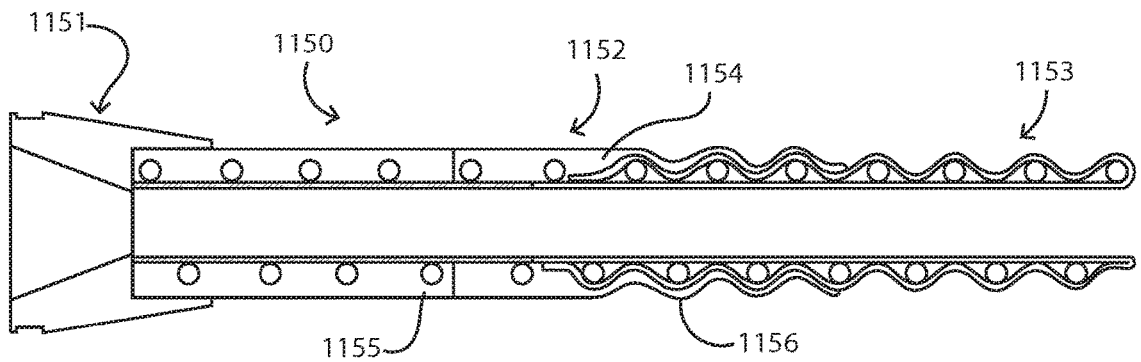
FIG. 27 shows the inner tubular layer being of ePTFE in a distal portion and of PTFE in a more proximal portion of the catheter; a butt joint is used in which the proximal liner is concentric within the distal liner.

In one configuration, the inner tubular layer is ePTFE in a distal portion and PTFE in a more proximal portion of the catheter as shown in FIG. 27 for a catheter 1150 having a proximal end 1151, an intermediate portion 1152, a distal portion 1153. There is a transition region 1154 in which the outer jacket a layer is merged into and, joined with an outer jacket of PTFE material in the intermediate portion and the transition region. The transition from ePTFE to PTFE may be achieved by a "butt" joint, in which the inner tubular layers of PTFE and ePTFE are in contact without overlap.

In another embodiment, a transition from inner tubular layer of ePTFE to PTFE occurs in a region of the catheter which is not subject to significant bending during use. In one configuration the device dimensions are suitable for placement in the neurovasculature, including M2, M1 and distal internal carotid arteries. Preferably, the transition from ePTFE to PTFE occurs proximal to the petrous segment of the ICA. In one configuration, the transition from an ePTFE to PTFE inner tubular layer occurs between 3 and 40 cm from the distal end of the catheter, preferably between 5 and 30 cm from the distal end, and more preferably at least 10 cm from the distal end.

In one configuration, the transition from inner tubular layer of ePTFE to PTFE occurs in a region proximal to a region of the catheter of rib and corrugation recess. In another configuration the transition from inner tubular layer of ePTFE to PTFE occurs proximal to the most flexible region of a rib and recess corrugate design, but still within a region of stiffer rib and recess corrugate design.

Figure 28:
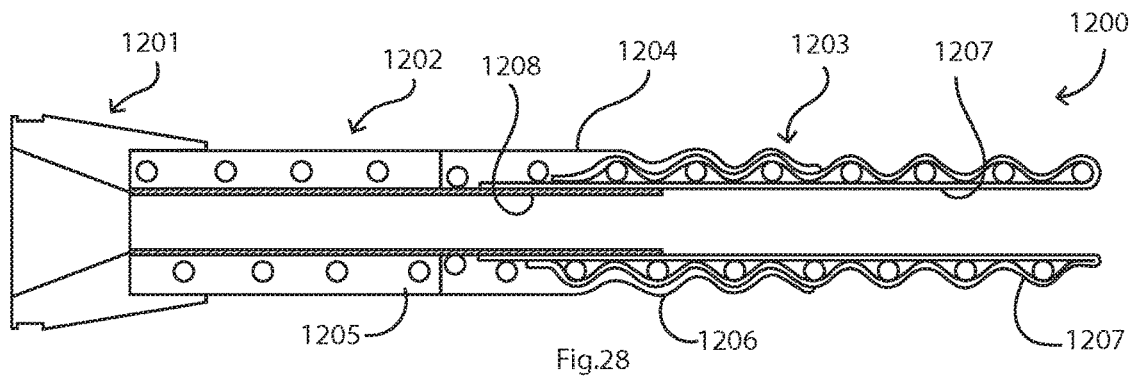
FIG. 28 shows the proximal region of rib and recess corrugation having an outer tubular layer comprised of a polymer material and a distal liner transitioning to different material; a lap joint is used in which the distal liner is concentric within the proximal liner.

In one embodiment the proximal region of rib and recess corrugate has an outer tubular layer comprised of a polymer material, as shown in FIG. 28. In one configuration the polymer material is a urethane or pebax. In one embodiment the polymer material is 80 A urethane. FIG. 40 shows a catheter 1200 having a proximal end 1201, an intermediate portion 1202, a distal portion 1203, and a transition region 1204. An ePTFE inner tubular layer (liner) 1207 transitions to a PTFE jacket 1205 in the intermediate portion within a corrugated section of the distal tip. A lap joint is used in which the PTFE tubular layer 1208 is concentric within the ePTFE tubular layer 1207.

In another embodiment the transition from ePTFE to PTFE may be achieved via a "lap" joint Wherein there is overlap of the tubular layers of ePTFE and PTFE. In one configuration the overlap between the PTFE and ePTFE is between 1 mm and 30 mm in length. The use of an overlap increases the area of interface for bonding thus improving the bond strength.

Figure 29:
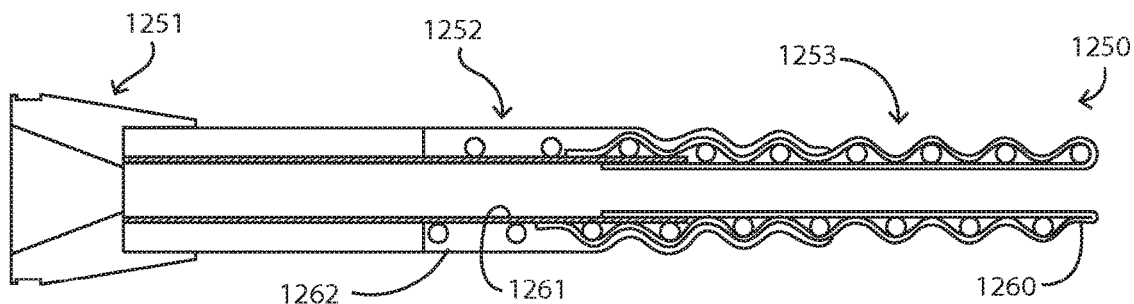
FIG. 29 shows that for a distance the ePTFE is concentric within the PTFE.

In one instance for a distance the ePTFE is concentric within the PTFE, as shown in FIG. 29. In this diagram a catheter 1250 has a proximal end 1251, and intermediate portion 1252, and a distal portion 1253. An inner liner 1260 is bent over at the distal end to form part of the outer jacket of the distal portion 1253. At a transition region between the intermediate portion 1252 and the distal portion 1253 the inner liner 1260 is within a tube of PTFE material 1261 with an overlap length of at least 2 mm, preferably at least 5 mm.

The tubular layer 1261 extends proximally within a jacket material 1262 in the intermediate portion 1252. This provides a configuration with an ePTFE inner tubular layer (liner) transitions to PTFE within a corrugated section of the distal tip. A lap joint is used in which the ePTFE tubular layer 1260 is concentric within the ePTFE tubular layer. 1261

In one configuration, a maker comprised of a helical coil of Platinum is present on the distal tip.

Figure 30:
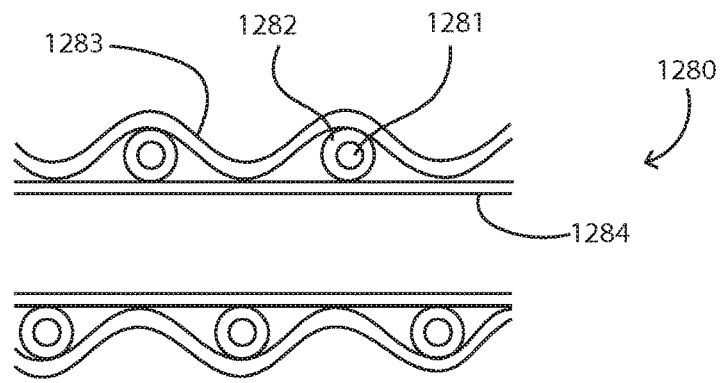
FIG. 30 shows a further arrangement of a helical support in the jacket in which the helical support is comprised of a tubular layer of Nitinol or other material over a radiopaque material such as Platinum; in this instance the coil may be floating or embedded.

In one embodiment, the helical support may be comprised of a radiopaque material such as Platinum wire. In another embodiment, to leverage the super elastic properties of Nitinol with radiopacity, the helical support may be comprised of drawn Nitinol tubing filled (such as Nitinol #1 DFT, Fort Wayne Metals) with Platinum or other radiopaque material. This would allow the physician to observe the distal tip behaviour under x-ray through the procedure. In one embodiment the helical support tube is comprised of at least 10% Platinum. FIG. 30 shows such an arrangement in which a catheter portion 1280 has a radiopaque helical coil 1281 around which there is a coating 1282, and there is a tubular layer 1283 over the outer jacket.

In one configuration, the radiopacity of the distal tip is further enhanced via a region in which the helical support pitch is reduced such that an area of greater density of radiopacity is achieved.

Figure 31:
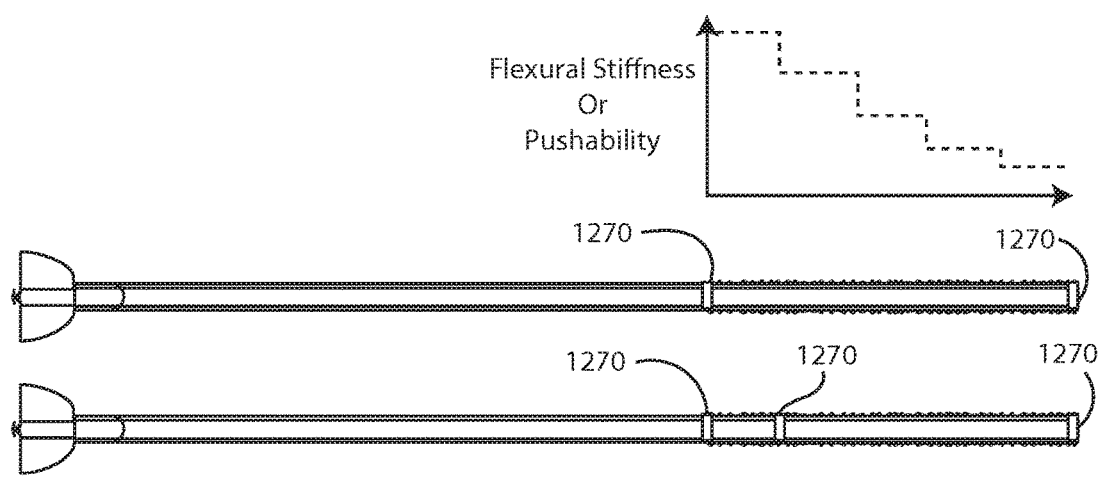
FIG. 31 shows catheters with radiopaque markers at various positions along its length.

FIG. 31 shows catheters with radiopaque markers 1270 at various positions along its length. Advantages and novel aspects are that allow the physician to ensure that more stiff regions the catheter are not placed in more delicate region of the vasculature. For example, a proximal marker at the start of the flexible distal tip can be used to define the region of the proximal catheter which should not be placed beyond the cervical C1 segment of the internal carotid artery. An intermediate marker can further be used to differentiate the end of a region of intermediate flexibility which should not be placed before, within, or beyond the cavernous segment C4. The region between the intermediate marker and distal marker establishes the region of highest flexibility which is suitable for placement in the C4-C7 regions of the internal carotid artery, and more distal vessels.

In one embodiment, in which the device is suitable for placement in the neurovasculature, the distal flexible tip length is at least 10 cm, and the un-lined distal section is at least 3 cm in length.

In another embodiment in which the device is suitable for placement in the peripheral vasculature, the
Aspiration Device including the Catheter.

A catheter of any example may be used for example for thrombectomy.

Recent clinical data has demonstrated that use of flow arrest using a balloon guide catheter can improve outcomes during thrombectomy procedures. This is done by:

Reducing flow towards the clot while the balloon is inflated proximal to the clot in the ICA. Reducing the flow reduces the potential for distal emboli to break off, or be carried distally, during the clot retrieval using a stentriever or aspiration catheter.

Providing a lumen for aspiration as the clot enters the BGC after it has been captured by a stentriever or aspiration catheter, and is dragged from the target site.

Figure 32:
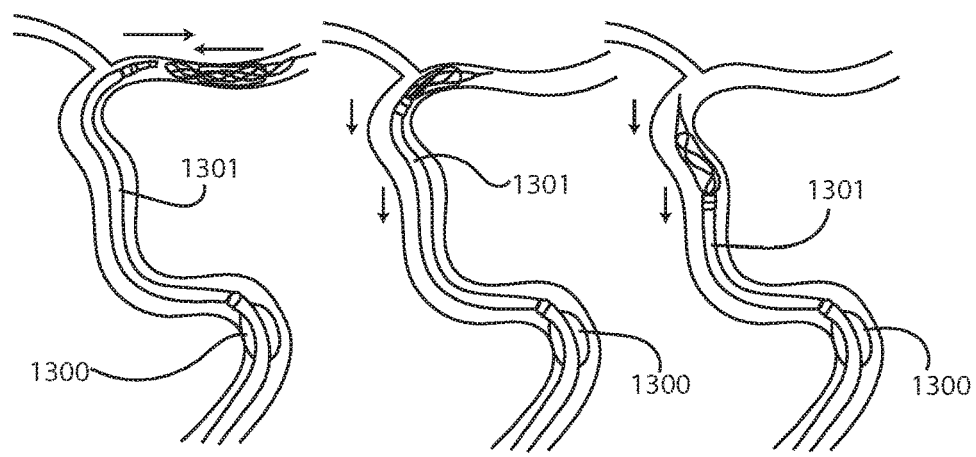
FIG. 32 is a series of diagrams showing a typical prior art setup of a balloon guide catheter in a thrombectomy procedure to provide proximal flow occlusion.

The prior art setup of balloon guide catheter in a thrombectomy procedure is shown schematically in FIG. 32, with a balloon 1300 and a tip 1301. Balloon guide catheters for use in thrombectomy procedures must facilitate the insertion of a microcatheter, and distal access catheter. In order to do this, the balloon guide must have an inner diameter in the range of SF or greater. Additionally, the catheter typically has an outer diameter in the range of 8F or 9F.

Existing catheter technology, at the dimensions described above, is extremely stiff. This is due to the catheter materials, design and architecture used, Therefore, the distal tip of the balloon guide catheter cannot be placed beyond the petrous segment. Excessive stiffness means the catheter is not flexible enough to track through the tortuosity of the distal ICA and other target vessels where the clot may be located, and there is a high potential for vessel damage or perforation.

Ideally, the tip of the balloon guide catheter should be as close to the clot as possible. This reduces the distance over which the clot must be dragged from the target vessel to the location of the balloon guide catheter tip. It may also enable the physician to directly aspirate the clot locally as the tip of the catheter can now engage the clot.

In some scenarios, remote aspiration of the clot is being performed using balloon guide catheters, while the balloon is inflated. Remote aspiration is a procedure in which the clot is aspirated without contact of the catheter tip with the clot. This works particularly well in a closed system where alternative flow pathways are not present. The success of this technique is often limited by the fact that the tip of the catheter can be a long distance from the clot.

A balloon catheter, whether used for PTA or embolic protection, is typically of a dual lumen, double layer construction along the length proximal to the balloon. This ensures there are two lumens; one for the passage of guide wires, catheters, or fluids, and one lumen for inflation. This dual layer construction is not always as flexible as desired, and is prone to kinking.

There is therefore a need for a balloon guide catheter which can provide flow arrest, but which also incorporates a very flexible distal portion which can track through a tortuous vessel, such as the distal ICA or as far as the M I or other vasculature.

In one embodiment a shaft or section with enhanced flexibility compared to the proximal section is present distal to the balloon of a balloon catheter. This flexible section enables the tip of the balloon to be placed more distally in the vasculature. This section of enhanced flexibility may be comprised of the types described in U.S. application Ser. No. 15/647,763, filed Jul. 12, 2017, titled "HIGH FLEXIBILITY, KINK RESISTANT CATHETER SHAFT," and U.S. Provisional No. 62/599,560, filed Dec. 15, 2017, titled "HIGH FLEXIBILITY, KINK RESISTANT CATHETER SHAFT" (both included in the Appendix), corrugate construction or other design.

This device may be designed so that the distal tip is flexible enough to reach and touch the clot for vacuum aspiration. The part which is distal of the flow restrictor (such as the balloon) includes the distal portion and preferably at least some of the transition portion. There may also be some of the transition portion proximally of the flow restrictor.

The length of this flexible section may vary such that it can reach specific anatomical locations, such as the distal internal carotid artery, terminus of the internal carotid artery, proximal MI, distal MI, proximal M2, distal M2, basilar, or vertebral vessels. This length may also help ensure that that while the tip of the catheter can reach the target vessel, the balloon does not pass the cavernous, or petrous segment of the ICA. Inflation of the balloon beyond these segments can cause vessel damage. The length of the flexible section may be between 1 cmn and 20 cm, preferably between 3 cm and 15 cm.

The outer diameter of this flexible tip may differ from the outer diameter of the proximal section of the catheter. In one embodiment the distal section has a larger diameter than the proximal section. In yet another embodiment the outer diameter has a diameter smaller than the diameter of the proximal section of the catheter. Variations such as a taper in the diameter of the distal section may also be used. Differing diameter distal sections can help to ensure access to specific vessels beyond the area to land the balloon.

Figure 33:
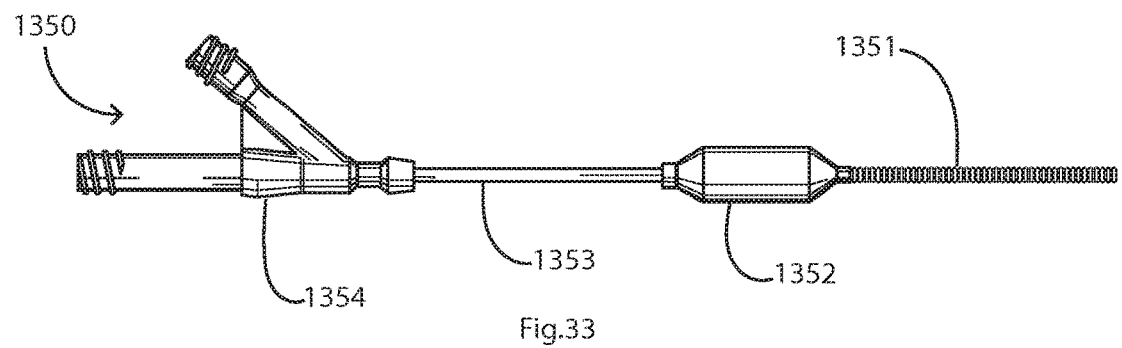
FIG. 33 shows a balloon catheter with an enhanced flexibility section on the distal tip.

FIG. 33 shows a device 350 with a flexible distal catheter tip 1351 extending from a balloon 1352, and proximally of which there is a catheter main section 1353 extending from a Y-piece 1354. FIG. 10 shows the balloon 352 inner layer inflation lumen 1360 and the balloon outer layer inflation lumen 1361.

Figure 34:
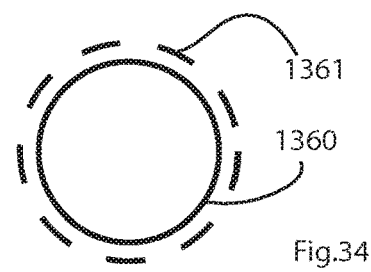
FIG. 34 is a diagram showing layers and lumens of a dual lumen balloon of the catheter of FIG. 33.

In one configuration, the outer layer of balloon inflation lumen may of enhanced flexibility while the inner layer of the balloon inflation lumen may be of a conventional construction comprising a single layer material, braided extrusion, coiled extrusion or other construction. These layers are shown schematically in FIG. 34, inner layer 1360 and outer layer 1361. In this way the pushability of the catheter may be maintained by the inner layer, while the outer layer mitigates compromise in terms of flexibility. Furthermore this construction will help to prevent kinking, since mechanics dictate that as the ratio of the inner diameter to the outer diameter of a tube increases, kink resistance is reduced. Use of the enhanced flexibility construction for the outer layer, traditionally more prone to kinking will solve this issue.

In another embodiment, a balloon catheter of dual layer construction comprises both inner and outer layer of the balloon inflation lumen of the enhanced flexibility construction. This will represent an ultra-flexible and kink resistant balloon catheter.

In other configurations, the proximal section may utilise other constructions to inflate the balloon such as a single lumen design with a vent hole and teak proof seal, a coaxial lumen or other design.

It should be noted that a balloon guide catheter, with a long distal tip capable of reaching a clot may be used as a thrombectomy device as follows:

Perform an angiogram to determine location of occlusion, and distance between petrous or cavernous carotid, and occlusion Choose a balloon catheter with distal tip length suitable to reach the clot, while ensuring the balloon inflation does not land beyond the petrous or cavernous carotid Navigate the distal tip of the catheter to the clot.

Inflate the balloon such that flow arrest is enabled, and alternative flow pathways which could reduce the effectiveness of the aspiration are minimised Apply a vacuum to the inner lumen of the catheter to aspirate the clot.

If the clot is retrieved, perform another angiogram through the balloon guide catheter or a diagnostic catheter.

Remove the balloon guide catheter.

Procedure is finished.

It may be noted that in the above method, the use of a large diameter distal tip, close to that of the target vessel will maximise the potential of complete clot ingestion.

Figure 35:
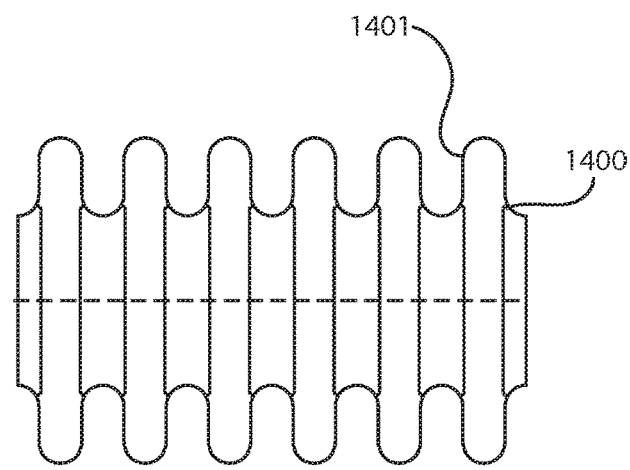
FIGS. 35 and 36 show corrugated tube tips for enhanced flexibility.
Figure 36:
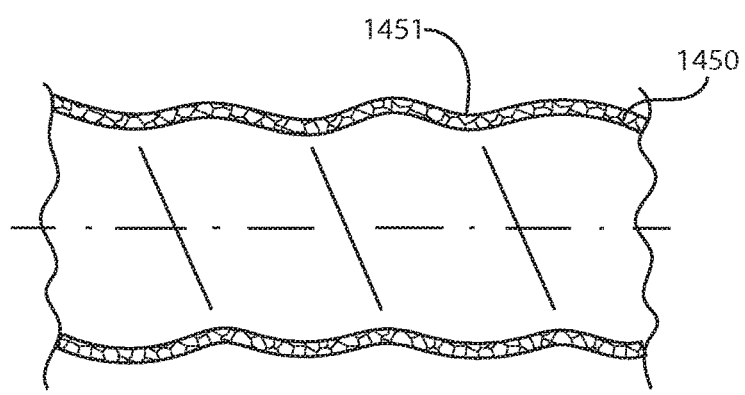

In yet another embodiment, enhanced catheter shaft flexibility and kink resistance may be achieved without additional helical wire support, but instead using a simple tubular construction with a corrugate architecture. The corrugations may be defined as adjacent circular depressions in the wall thickness of the tube, or as a continuous helical depression as shown in FIGS. 35 and 36 respectively. In these diagrams the tip has an outer layer 1400 with corrugations 1401 (FIG. 35) and an outer layer 1450 with more shallow corrugations for desired flexibility.

The device may be designed so that the distal tip is flexible enough to reach and touch a clot for vacuum aspiration. The typical target vessels are the M1, M2, M3, distal ICA.

The distal tip should be long enough to reach the target vessel, while also ensuring that the balloon does not pass the petrous segment of the internal carotid artery (known as C2). This is because the vessels and surrounding tissue beyond the petrous segment are prone to damage which can have catastrophic consequences.

It is preferable to ensure that the location of the balloon when inflated is within C1 segment of the carotid artery. It is also preferable that the balloon be distal to the external carotid artery to ensure effect flow restriction and or flow reversal. The length of the flexible section may be between 1 cm and 20 cm, preferably between 3 cm and 20 cm.

FIG. 37 left image shows an Angiogram demonstrating the external carotid, common carotid and internal carotid artery (ICA), including the C1 and C2 segments, and right image shows acceptable positioning of the balloon (2282, in a catheter 2280 proximal of a distal end 2281. It should not be inflated past the C2 segment. The distal tip length of the catheter should be long enough to reach the clot while ensuring safe position within or proximal to the C2 segment of the ICA.

Any or all the embodiments described above to refine the transition from the stiffness of the proximal portion of the distal tip to the most distal portion may be used.

The proximal shaft must serve two functions and have at least two lumens; one for balloon inflation and a main lumen for delivery of fluids and devices, and for aspiration. The flexible tip only requires one lumen, therefore has potential to have a larger lumen than the proximal section. In one embodiment the inner diameter of the flexible tip is the same inner diameter as the proximal shaft.

In another embodiment the proximal and distal shaft have the same outer diameter, and the proximal shaft has two concentric lumens, in which the central lumen diameter is less than that of the flexible distal tip as shown in FIG. 38. This drawing shows a balloon guide catheter 2300 with a flexible corrugated distal tip 2302 and a balloon 2301. In this incidence the inner diameter of a proximal shaft lumen 2303 is less than that of the flexible corrugated distal tip 2302. The proximal and distal shafts have the same outer diameter.

In another embodiment the inner diameter of the proximal shaft is the same as that of the flexible distal tip. In yet another embodiment, the outer diameter of the distal tip is smaller than that of the proximal shaft. The distal tip inner diameter may be the same as, or smaller than, the inner diameter of the proximal shaft. FIG. 39 shows a catheter 1400 with a balloon 2401 and a distal portion 2402 having a smaller outer diameter than the proximal portion 2403.

In one configuration, the distal tip is comprised of a flexible corrugate section distally, and a non-corrugated section proximally. FIG. 40 shows a catheter 1500 with a non-corrugated proximal region 2501 of the distal region 2502.

Figure 41:
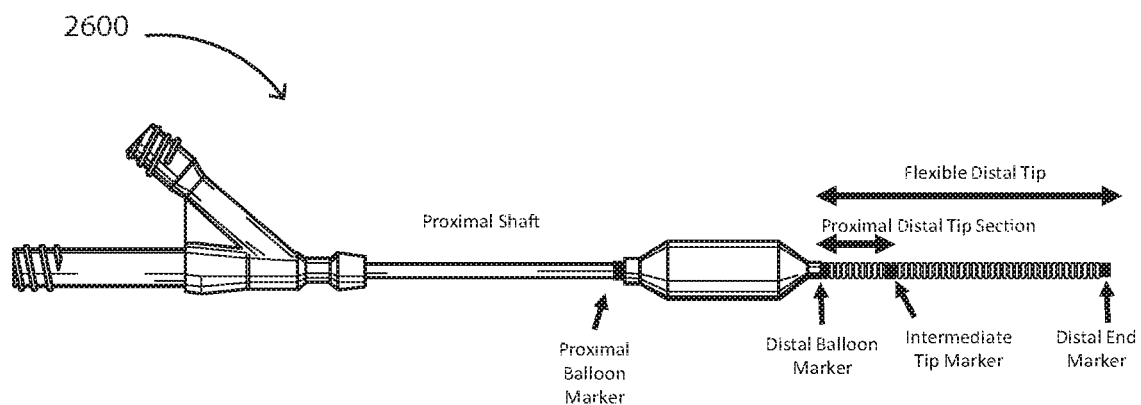
FIG. 41 shows a catheter device with a radiopaque marker at the distal end of the flexible distal tip.

In one configuration, as shown in FIG. 41 for a catheter device 2600 a radiopaque marker is present at the distal end of the flexible distal tip. Markers are also present immediately distal and or proximal to the balloon to define its location. An additional intermediate distal marker may be present within the distal tip to define a proximal region of increased stiffness unsuitable for placement in distal to the C2 segment of the ICA.

In one configuration, the balloon catheter is suitable for use via direct carotid access. In this case a shorter proximal shaft will improve ergonomics for the physician. In this instance the length of the catheter shaft proximal to the balloon does not exceed 40 cm, and preferably does not exceed 30 cm.

Flow Restriction Using Larger Bore Catheter via Near Vessel Occlusion or Wedging The embodiments described above enable the physician to place larger bore catheters more distally than has been possible using conventional catheter technology. However, it may not be possible to place a larger catheter in the target vessel due to the vessel diameter being smaller than the catheter itself. In this instance a larger catheter may be used to achieve flow restriction.

In some instances, additional vessels are present which perfuse the treatment area. For example, in the case of the anterior cerebral artery, proximal occlusion using a balloon guide catheter placed in the ICA does not prevent inflow to the target treatment site. This is also a problem in posterior stroke where there are two significant inflow vessels (left vertebral artery and right vertebral artery), and the target treatment site is the basilar artery or posterior communicating artery.

Figure 42:
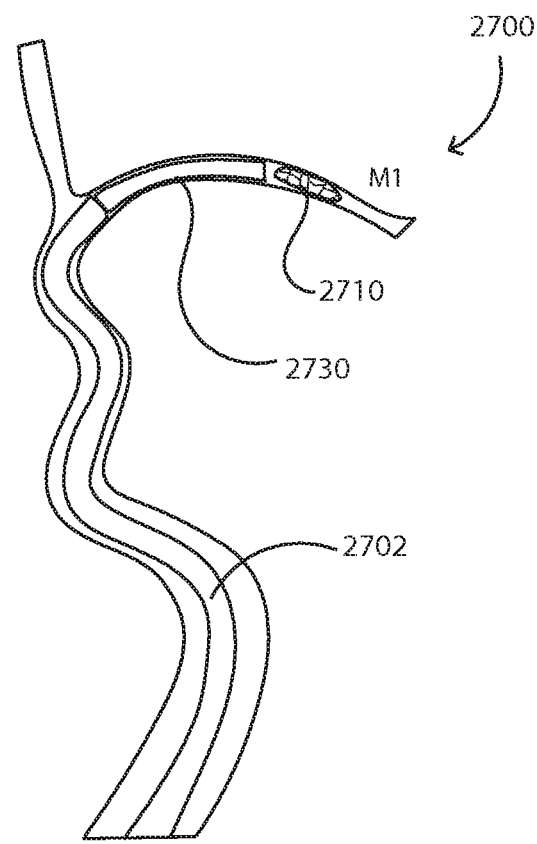
FIG. 42 shows a mother and daughter catheter arrangement wherein the larger catheter is used to occlude inflow to the target vessel, while the smaller catheter is used to retrieve the clot.

In one embodiment a system is comprised of a "mother" and "daughter" catheter, in which significant flow restriction, or flow arrest, may be achieved by placing or wedging a large bore highly flexible mother catheter in a vessel location proximal to the target treatment site. A smaller daughter catheter may then be passed through the parent catheter to the treatment site. In this instance a proximal balloon for flow restriction is not required. Near occlusion of the vessel, without wedging the catheter, will dramatically reduce flow also. This is shown in FIG. 42, in which there is a large catheter 2702 and a smaller catheter 2703 for aspiration of a clot 2701. Large bore highly flexible catheters can enable the most distal flow arrest possible In other instances, such as embolization, flow restriction using a larger bore catheter may also be advantageous. For example, in embolization, where embolization of non-target vessels is a major concern, additional embolization procedures are often used occlude adjacent non-target vessels. Non-target embolization can cause non-target vessel occlusion, or the delivery of a drug to non-target tissue. This may be avoided if a larger bore highly flexible catheter is placed distally in the vessel feeding the target region of delivery of the embolic such that the catheter tip is wedged. Upon injection of the embolic, the wedged condition prevents retrograde flow of the embolic, thus preventing non-target embolization. Furthermore, the pressure gradient within the vessel is a reflection of the proximal injection pressure, rather than the hemodynamic pressure, giving the physician full control of the delivery of the embolic.

Figure 43:
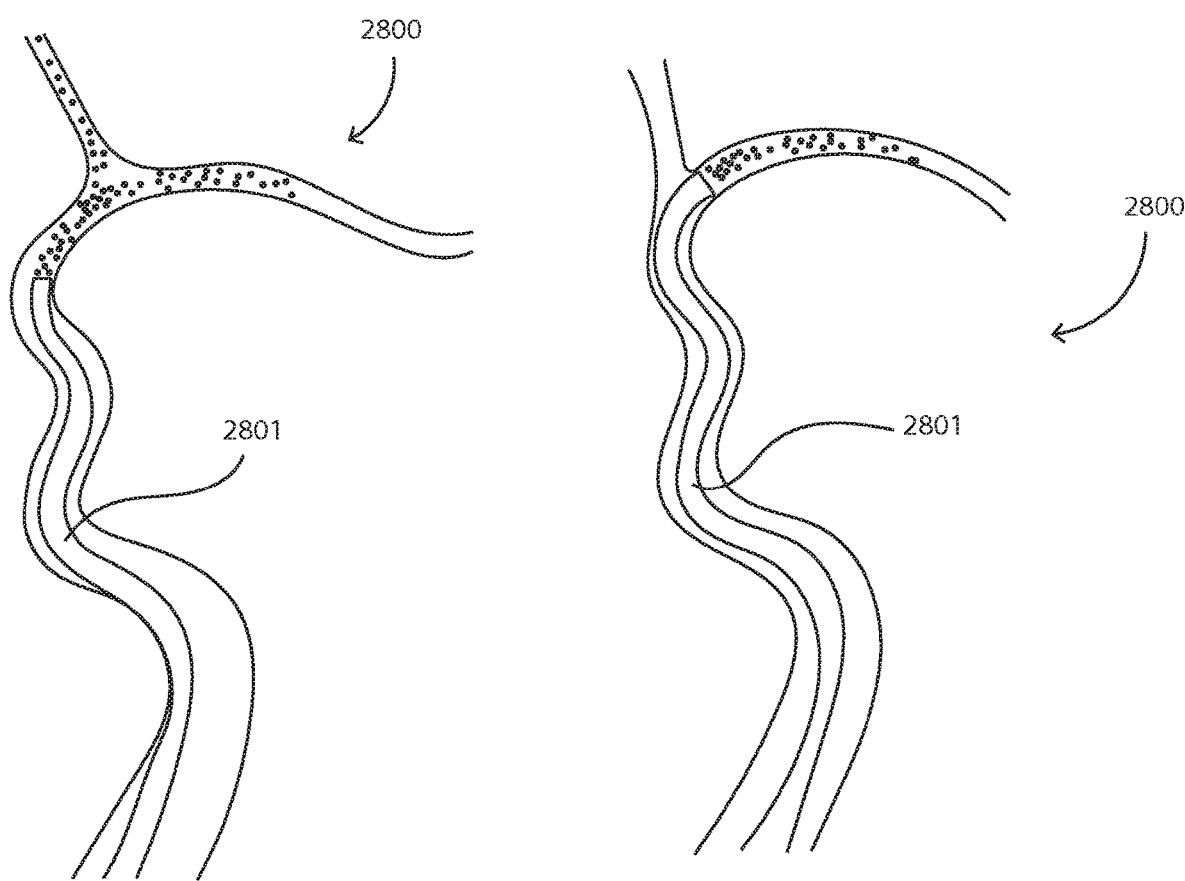
FIG. 43, left diagram, shows the use of a small catheter unable to reach a distal target vessel (right) during delivery of a drug or embolic and the resulting undesired delivery to a non-target vessel (top left vessel); and the right hand diagram shows a method wherein a highly flexible large diameter catheter is chosen to effectively occlude the target vessel, and can be placed beyond the non-target vessel, so delivery of the embolic only occurs to the target vessel; it is preferable that the catheter is wedged in the target vessel.

FIG. 43 shows such a configuration, in a catheter 2800 having a distal portion 2801, Left shows the use of a small catheter unable to reach a distal target vessel (right side vessel) during delivery of a drug or embolic and the resulting undesired delivery to a non-target vessel (top left vessel) The right hand diagram shows the use of a method wherein a highly flexible large diameter catheter is chosen to effectively occlude the target vessel, and can be placed beyond the non-target vessel, so delivery of the embolic only occurs to the target vessel. It is preferable that the catheter is wedged in the target vessel.

Furthermore, the distal nature of the vessels targeted in embolization procedures means that often, only microcatheters are capable of entering the vessels today. This limits the type of embolic which can be used (e.g. 018 microcoils may need to be used where larger 035 coils or a plug would e preferred, or the desired particle becomes clogged in the only microcatheter capable of entering the vessel). The technical success of these procedures (in particular embolization for BPH) is also limited by the inability to place larger support catheters distally.

A corrugated catheter section with or without a transition arrangement may be used as a proximal section of a catheter in order to provide flexibility about a particular bend, for example, as an access sheath to provide controlled flexibility about the iliac arch. The configurations may could also be incorporated into a more flexible a urethral stent design or Foley-style catheter, and for a flexible endoscope of corrugate wall.

The device may be used to block blood flow before precise delivery of an embolic agent to region of the vasculature, tumour, or organ.

Aspiration System with Pressure-Controlling Pump

Aspiration has been shown to be safe for the retrieval of clots from the cerebral vasculature. However, technique suffers from a number of limitations. In particular, it is frequently the case that the clot cannot be ingested at the target treatment site. This is particularly the case for harder, larger diameter, and longer clots.

If not completely ingested, the physician will attempt to withdraw catheter and attached clot from the patient under continuous vacuum. This manoeuvre carries risk, is time-consuming, and means the physician has lost access to the target vessel.

If following angiography the physician determines that the target region has not been reperfused, additional attempts must be made to retrieve the clot. Up to five attempts, known as passes are typically required. On average two attempts are required. In 20% to 30% of cases, aspiration is not successful after multiple attempts, and physicians will switch to the use of a stent retriever (Almandoz et al. 2015; Lapergue et al. 2017; Blanc et al. 2017; Mohlenbruch et al. 2016). This further increases procedural time and cost.

As the physician withdraws the catheter proximally towards the access site (typically femoral or radial artery), there is a likelihood that some or all of the clot may break off. These fragments of clot, are known as emboli. Distal emboli lead to poor reperfusion outcomes when assessed under angiography or other imaging. Poor reperfusion, as defined by the TICI scale, is associated with worse patient outcomes.

Another limitation of the aspiration technology is that it is not always possible to advance the catheter tip to the face of the clot. This is due to the extreme tortuosity which may be present in the patient, meaning that often only small diameter catheters such as microcatheters can reach the clot. Larger bore catheters are known to have a greater potential to aspirate the clot, but are frequently too stiff to navigate to the clot face. In this instance, the physician may use a smaller bore catheter, but is less likely to successfully aspirate the clot.

Depending on internal diameter of the catheter, and properties of the clot (diameter, length, hardness/durometer, elasticity etc.), there is a limit to the amount of clot which can be aspirated into the catheter lumen. At this limit the catheter may be described as being clogged. Large lumen catheters can aspirate more clot than small lumen catheters without becoming clogged. During aspiration, the limit to the amount of clot which can be aspirated may be reached before a complete vacuum is reached. This implies that the application of further vacuum does not necessarily increase the amount of clot which is aspirated once a certain limit is reached. This is shown schematically in FIGS. 44(a) to 44(e), showing a catheter tip 3500 being used to attempt aspiration of a clot 3501. As illustrated, there is incomplete aspiration. It is a limitation of existing vacuum technology (vacuum pumps and syringes) that the applied vacuum is not engineered to prevent clogging, or maximise efficiency of aspiration.

Based on the problems outlined above, it is desirable to enable the clot to be ingested at the target site in a single manoeuvre. This will save time, reduce procedural complexity, and minimise potential for clot fragmentation during clot retrieval.

Figure 45:
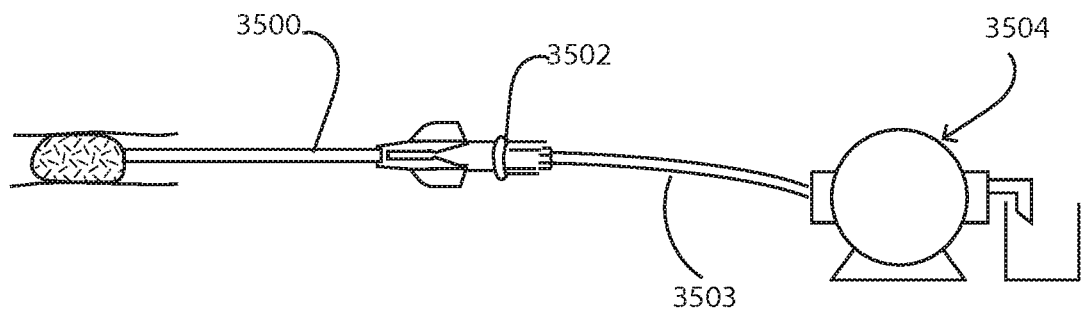
FIG. 45 shows a setup used for aspiration of a clot or other material from the body using a pump.

A pump is disclosed, for use in connection with a catheter such as described above in any embodiment, to aspirate clots or other materials from a blood vessel or other region of the body. An aspiration device is shown schematically in FIG. 45, having a catheter 3500, a guide 3502, tubing 3503, and a pump and reservoir assembly 3504.

The invention utilises control and/or, variation of the vacuum pressure and/or, fluid displacement during aspiration to improve the efficiency of aspiration. Variations in pressure and/or fluid displacement at the catheter tip can help achieve the following:

Prevent clogging of the catheter

Promote maceration and deformation of the clot to enable it to travel through the lumen The pump 3504 may provide a negative fluid displacement thereby decreasing pressure (enabling a vacuum) or positive displacement, thereby increasing pressure. The pump is connected to a catheter, enabling application of a positive or negative pressure the catheter lumen. The pump incorporates a sensor which measures the pressure in the catheter lumen.

The magnitude of this pressure may be used to decide whether a vacuum or pressurizing signal should be applied to the catheter. Based on the measured pressure, the pump may change direction hence altering the pressure and fluid displacement.

Figure 46:
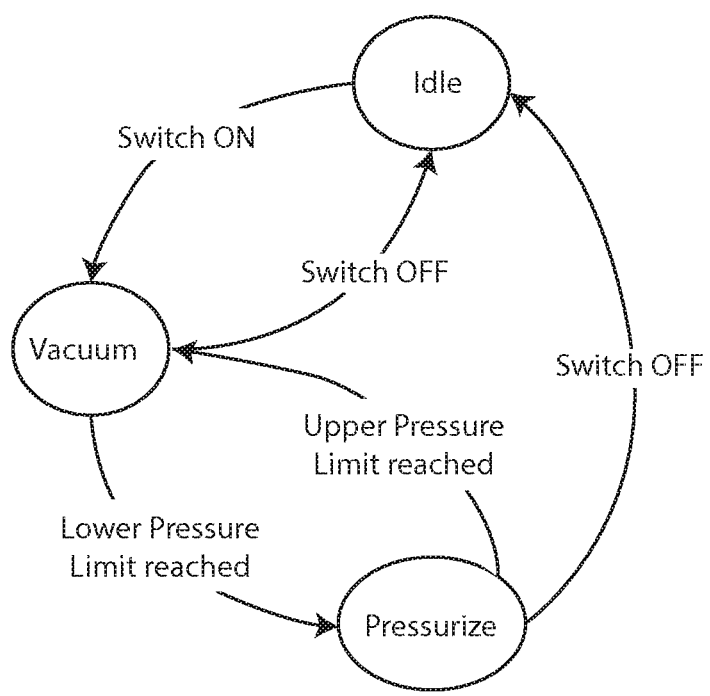
FIG. 46 is a flow diagram showing steps including pressure monitoring to establish whether the pump should apply vacuum or pressurize during the aspiration procedure.

In one embodiment, shown schematically in the form of a state diagram in FIG. 46, the pump uses defined upper and lower limits to decide whether to apply a vacuum or pressurize. These limits enable the catheter to cyclically ingest and if required expel, at least some of the clot. This deformation of the clot improves the efficiency of the aspiration, and prevents clogging of the catheter.

For the purposes of explanation, the initial pressure is defined as 0 in-Hg in all diagrams before the pump is switched on FIG. 47 (a). In reality, a non-zero pressure is present due to blood pressure. This may be in the region of 60 to 120 mm-Hg (2.4-4.8 in-Hg).

The pump will continuously measure the pressure within the catheter lumen during the procedure. This measurement will be arterial pressure if the pump is switched off. Once the pump is switched on, and it begins to draw some vacuum a negative pressure will be measured, FIG. 47 (b). In the absence of an occlusion or partial occlusion of the catheter tip, this will be a nominal reading, representing free-flow of fluid through the catheter). Once the catheter is advanced and engaged with the clot, an increase in the vacuum is observed, FIG. 47 (c).

Initially when switched on the pump applies a vacuum enabling the catheter to ingest some of the clot, FIG. 47 (d). While further increases in the vacuum ingest more of the clot, FIG. 47 (e), the efficiency of increases in the vacuum pressure in ingesting more clot is reduced, FIG. 47 (f). For this reason, the pump will reverse at some Low Limit of pressure, FIG. 47 (g). The Low Limit is defined such that during vacuum, a portion of the clot has been aspirated but not so much that the clot has become irreversibly clogged. An important aspect is that the lower limit of vacuum can be set well above the full vacuum pressure of −760 mmHg to prevent ingestion of too large a clot that could clog the catheter. In one embodiment, the Lower Limit is set to between −100 mm-HG and −200 mm-Hg. In another embodiment the Lower Limit is set to between −200 mm-HG and −300 mm-Hg. In another embodiment the Lower Limit is set to between −400 mm-HG and −500 mm-FIg. In another embodiment the Lower Limit is set to between −600 mm-HG and −700 mm-Hg.

The direction of fluid displacement of the pump is now reversed. Upon reversal, the catheter will begin to pressurize, thereby increasing the pressure measured, FIG. 47 (g). As the catheter is pressurized (vacuum is reversed), the load which was applied to ingest the clot will be reduced, thereby unloading the clot, and even allowing some or all of the clot to be pushed distally towards the catheter tip FIG. 47(h). During this loading/unloading the clot is being macerated and accordingly becomes more "free" within the catheter.

The pressure is further increased until a High Limit is reached. In one embodiment this High Limit is defined such that the ingested clot may not be completely expelled from the catheter.

Additional cycling of the clot between the Low Limit and high limit (FIG. 47 (i) to (j)) further macerates the clot enabling a greater amount of the clot to be ingested for the same Low Limit of vacuum (FIG. 47 (m)), with eventual complete ingestion of the clot, FIG. 47 (n).

In one embodiment the High Limit is a negative pressure. In another embodiment, the high limit may be 0 mmHg. In yet another preferred embodiment, the High Limit is a positive pressure (FIG. 48 (a) to (c).

In the absence of a pressure signal from the pump the presence of intra-vascular blood pressure means there is a force present which supports transport of material from the distal tip of the catheter towards the pump. In one embodiment, an initial blood pressure reading may be taken before the procedure is initiated. This reading may be used to calculate the precise High Limit value required. The mean blood pressure, systolic blood pressure, or diastolic blood pressure may be used. A novel aspect of this pump system is the incorporation of feedback into the pump algorithm in order to produce more effective pressure cycling. That is to say, the ability of the pump to measure the condition in the pump (e.g. pressure or fluid displacement), and continue or alter its behaviour.

Figure 50A:
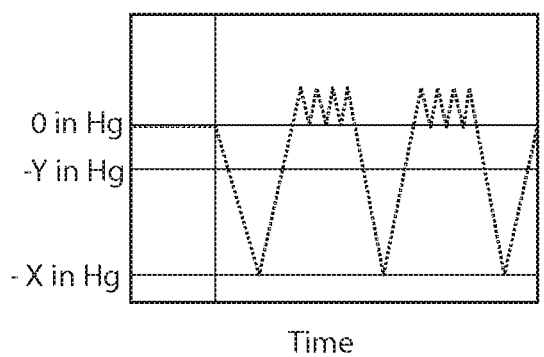
FIGS. 50(a) and 50(b) are plots showing shake signals.
Figure 50B:
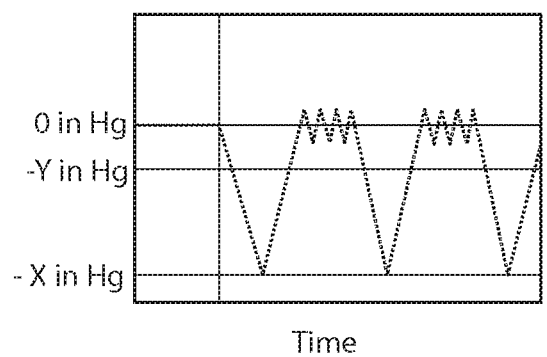

In one embodiment, the applied pressure signal incorporates an oscillation or "shake" signal. The shake signal implies the application of pulse cycling between two pressure limits as shown in FIGS. 50(a) and (b). The signal provides acute aspiration of the clot in order to cause deformation and, or, fragmentation of the clot to improve transport through the catheter. Another aspect is the incorporation of rate based cycling of a negative and positive pressure signal. Oscillating frequencies can be defined that may cause the elastic modulus of a clot to be exceeded, thereby, fragmenting the clot in the catheter and promoting easier transport.

Figure 49:
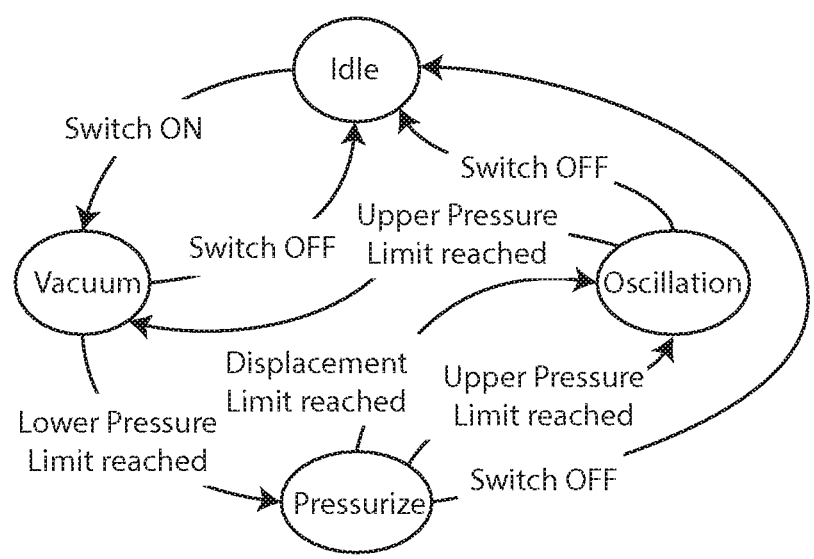
FIG. 49 is a flow diagram showing method steps for positive oscillation or shake signals.

The addition of this oscillation is shown in the form of the state diagram in FIG. 49.

In one embodiment the shake signal may be initiated for a predefined number of cycles. In another embodiment, the shake signal may be used until the pressure has returned to blood pressure. In this instance the material in the catheter can effectively flow without significant resistance. In another embodiment, this shake signal may be initiated based on a specific pressure indicative of catheter occlusion or partial occlusion, and terminated based on measurement of pressure within the catheter indicative of free-flow, or partial occlusion.

While the figures generally show a triangular wave form of pressure with respect to time, it should be pointed out that this may not be the case in reality. The graphs are intended to illustrate the directional changes in pressure which are initiated and controlled by the invention.

For example depending on the clot properties, and speed of activation or reversal of the pump, the signals may be more square, saw-tooth, or sinusoidal in form. Furthermore, the resulting pressure—time relationship may not have any repeating unit at all.

In one embodiment the invention includes both an oscillation or shake signal in the vacuum and positive pressurize signals. This is shown schematically in FIGS. 51(a) and 51(b). In yet another embodiment, the system my incorporate only a vacuum oscillation.

A range of Lower Pressure and Higher-Pressure limit values may improve efficiency of clot transport compared to static aspiration technology. In one embodiment it is preferable to specify a Lower Pressure limit such that the amount of clot which can be ingested is maximised for a single cycle. In another embodiment, it is preferable that the Lower Pressure limit is specified such that the amount of clot which is ingested in a single cycle is not maximised, but instead represents an intermediate condition between a small amount of clot ingestion and maximum clot ingestion. Real numbers will be added in the future based on experiment.

In another embodiment, the lower limit may be defined in real-time. In one embodiment, a change in the rate of change of the pressure during the vacuum cycle may be used. For example, as the catheter becomes clogged, there is generally a rapid increase in the vacuum pressure. This sudden change in vacuum pressure may be used as a signal to switch the direction of the pump.

Similarly, the upper pressure may be defined based on a sudden change in the pressure during the pressurize cycle. In one embodiment this may be defined in order to identify a condition where the catheter is de-clogged.

It should be appreciated that the upper and lower limits may be defined by a combination of rate of change in pressure, or specific pressure value, or a combination of both.

In another configuration, a flow displacement, or flow meter is incorporated. This may be used to define upper and lower limits to establish the direction of the pump (aspiration or vacuum). In one embodiment the flow meter can detect if there is no fluid displacement, which is suggestive of catheter clogging.

In another embodiment, the pump may use positive and negative fluid displacement to alternately infuse and aspirate the catheter. In one embodiment, the ratio of the infuse-to-aspirate cycle may be between 0.01 and 0.99. Preferably the ratio will between 0.1 and 0.9, or more preferably between 0.4 and 0.9.

In one configuration, the pump is a sterile unit, which can be used within the sterile field, or on the patient table adjacent to the patient. This enables the physician to perform all manoeuvres without the requirement of a technician outside the sterile field. The unit may be single use and disposable.

In one configuration, the pump incorporates a peristaltic pump mechanism. This ensures that there is no blood contact with the pump parts. The pump may incorporate a reservoir for collection of aspirate. FIGS. 53(a) and 53(b) show a pump and components. Shown are a housing connecting a tube, an on-off switch, a battery pack, a pulsatile pump, and a motherboard. The pressure sensor is connected to the tube-lumen, which is connected to the catheter, thereby enabling pressure measurement within the catheter.

In one embodiment the pump incorporates a series of LEDs or indicators. These are intended to provide feedback to the physician based on the catheter tip and clot interaction condition. This is provided by the pressure within the catheter. For example, the pressure range associated with free-flow within the catheter, or partial occlusion, or complete occlusion, aspirating or clogged.

Furthermore, the indicators may be used to indicate to the physician that the pump is in the oscillation or shake condition.

A method is disclosed whereby the physician uses the feedback from the indicators to define the required adjustment of the catheter tip.

Place catheter tip adjacent to the clot. Switch on the pump. If the pump indicates free flow is observed the catheter should be moved distally to further engage the clot. If the catheter is aspirating with partial or complete occlusion the physician waits until the pump has free-flow again. The physic again moves the catheter tip distally to engage the next piece of clot. In this way the entire vessel can be cleaned of clot. In the event that the pump becomes clogged a signal may be provided to the physician that the traditional catheter withdrawal technique may be appropriate.

The embodiments described within this filing are in general aimed at enabling the physician to access regions of the body which provide a challenging anatomy, with highly flexible corrugated catheters. The catheter designs are optimised by way of transitions, and the addition of other elements, such as flow restrictors and a highly effective pump. The ability to make larger catheters while maintaining this type of controlled flexibility enables improved therapy, such as clot removal, embolic delivery to the body.

The invention is not limited to the embodiments described but may be varied in construction and detail.

The invention claimed is:

1. A catheter, comprising:
a sheath having a longitudinal axis and defining a lumen, the sheath having a proximal end, a distal end, and a transition portion between the proximal end and the distal end;
a reinforcing structure surrounding the lumen; and
a plurality of helical corrugations disposed only in the transition portion of the sheath and the distal end of the sheath, wherein each of the plurality of corrugations are defined by a plurality of valleys and a plurality of peaks,
wherein a distance from at least one valley of the plurality of valleys to the longitudinal axis is less than a distance from a radially outermost surface of the reinforcing structure to the longitudinal axis,
wherein the sheath includes a jacket including a first material, and an inner liner including a second material different from the first material,
wherein a distal end of the inner liner includes an ePTFE material and a proximal end of the inner liner includes a PTFE material, wherein a transition from the proximal end of the inner liner to the distal end of the inner liner is in the proximal end of the sheath, and
wherein the proximal end of the inner liner and the distal end of the inner liner are connected together by a lap joint.

2. The catheter of claim 1, wherein a width of at least one of the plurality of corrugations is 15%-45% of a pitch of the plurality of corrugations.

3. The catheter of claim 1, wherein the jacket surrounds the inner liner, and wherein the reinforcing structure is contacting both the jacket and the inner liner.

4. The catheter of claim 3, wherein the reinforcing member includes a helical support coiled around the lumen of the sheath, wherein a cross-section of the helical support is circular, and wherein a pitch of the helical support in the proximal end of the sheath is different from a pitch of the helical support in the distal end of the sheath.

5. The catheter of claim 1, wherein the reinforcing structure is disposed entirely within the jacket such that the jacket surrounds an entirety of the reinforcing structure.

6. The catheter of claim 1, wherein the plurality of corrugations are disposed only in the jacket of the sheath, wherein a proximal end of the jacket includes a pebax material, and wherein a distal portion of the jacket has a durometer of approximately 80 A.

7. The catheter of claim 1, wherein a depth of each of the plurality of corrugations is a distance between a peak and a valley of each of the plurality of corrugations, wherein the depth of at least one corrugation of the plurality of corrugations in the distal end of the sheath is at least 60% of a thickness of the sheath, and wherein the thickness is a distance between a radially outermost surface of the sheath and a radially innermost surface of the sheath.

8. The catheter of claim 1, wherein the reinforcing structure is disposed between adjacent valleys of the plurality of corrugations.

9. A catheter, comprising:
a sheath defining a lumen and including a plurality of corrugations, the sheath including:
an inner liner having a distal end and a proximal end, and
a jacket surrounding the inner liner; and
a reinforcing structure surrounding the lumen,
wherein a distance from a radially innermost surface of at least one corrugation from the plurality of corrugations to a longitudinal axis of the sheath is less than a distance from the longitudinal axis of the sheath to a radially outermost surface of the reinforcing structure,
wherein a width of at least one corrugation of the plurality of corrugations is at least 20% of a thickness of the jacket,
wherein the distal end of the inner liner includes an ePTFE material and the proximal end of the inner liner includes a PTFE material,
wherein a proximal end of the jacket includes a pebax material, and
wherein a distal portion of the jacket has a durometer of approximately 80 A.

10. The catheter of claim 9, wherein the sheath includes a proximal end, a distal end, and a transition portion between the proximal end and the distal end, and wherein the reinforcing structure is disposed only within the jacket of the sheath.

11. The catheter of claim 10, wherein the reinforcing structure extends in the proximal end, the distal end, and the transition portion of the sheath.

12. The catheter of claim 9, wherein the jacket includes a distal end and a proximal end, wherein the proximal end of the jacket includes a smooth outer surface, and wherein the at least one corrugation of the plurality corrugations is at least 60% of the thickness of the jacket.

13. The catheter of claim 9, wherein the plurality of corrugations is provided only in a distal end of the sheath and a transition portion of the sheath, and wherein a portion of the inner liner extending parallel to the plurality of corrugations when the sheath is approximately parallel to the longitudinal axis of the sheath includes only the ePTFE material.

14. The catheter of claim 9, wherein a depth of a first corrugation from the plurality of corrugations is different from the depth of a second corrugation from the plurality of corrugations, and wherein a depth of at least one of the first corrugation or the second corrugation is at least 70% of a thickness of the sheath.

15. A catheter, comprising:
- a sheath having an inner liner, an outer jacket, and defining a lumen and including a plurality of corrugations; and
- only one wire surrounding the lumen in a portion of the sheath including the plurality of corrugations, wherein the only one wire contacts both the inner liner and the outer jacket,
- wherein a distance from a radially innermost surface of one corrugation from the plurality of corrugations to a longitudinal axis of the sheath is less than a distance from an outermost surface of the one wire to the longitudinal axis of the sheath,
- wherein a depth of each of the plurality of corrugations is a distance between a peak and a valley of each of the plurality of corrugations, and the depth of at least one corrugation of the plurality of corrugations at a distal end of the sheath is at least 50% of a thickness of the sheath,
- wherein the thickness is a distance between a radially outermost surface of the sheath and a radially innermost surface of the sheath,
- wherein a distal end of the inner liner includes an ePTFE material and a proximal end of the inner liner includes a PTFE material, and
- wherein a pitch of the only one wire in a proximal end of the sheath is different from a pitch of the only one wire in the distal end of the sheath.

16. The catheter of claim 15, wherein a width of at least one of the plurality of corrugations is 15%-45% of a pitch of the plurality of corrugations.

17. The catheter of claim 15, wherein the sheath includes a jacket and an inner liner, wherein the jacket surrounds the inner liner, and wherein the plurality of corrugations are disposed only in the jacket of the sheath.

18. The catheter of claim 17, wherein the inner liner includes an ePTFE material.

19. The catheter of claim 15, wherein the sheath includes a proximal end, a distal end, and a transition portion connecting the proximal end and the distal end, wherein the plurality of corrugations are disposed only in the distal end of the sheath and the transition portion of the sheath, and wherein the depth of the at least one corrugation of the plurality of corrugations at the distal end of the sheath is at least 70% of the thickness of the sheath.

20. The catheter of claim 15, wherein the depth of at least one of the plurality of corrugations in the distal end of the sheath is greater than the depth of at least one of the plurality of corrugations in the transition portion of the sheath.

21. The catheter of claim 15, further comprising a braided extrusion surrounding the lumen in a portion of the sheath proximal to the plurality of corrugations.

\* \* \* \* \*